US011116680B2

(12) United States Patent
Derenne et al.

(10) Patent No.: US 11,116,680 B2
(45) Date of Patent: Sep. 14, 2021

(54) PATIENT SUPPORT APPARATUS FOR CONTROLLING PATIENT INGRESS AND EGRESS

(71) Applicant: Stryker Corporation, Kalamazoo, MI (US)

(72) Inventors: Richard A. Derenne, Portage, MI (US); Brian J. Tessmer, Mattawan, MI (US); Justin R. Murray, Portage, MI (US); Kurosh Nahavandi, Portage, MI (US); Cory P. Herbst, Shelbyville, MI (US)

(73) Assignee: Stryker Corporation, Kalamazoo, MI (US)

( * ) Notice: Subject to any disclaimer, the term of this patent is extended or adjusted under 35 U.S.C. 154(b) by 344 days.

(21) Appl. No.: 16/134,004

(22) Filed: Sep. 18, 2018

(65) Prior Publication Data

US 2019/0083337 A1   Mar. 21, 2019

Related U.S. Application Data

(60) Provisional application No. 62/560,407, filed on Sep. 19, 2017.

(51) Int. Cl.
  *A61G 7/015*  (2006.01)
  *A61G 7/018*  (2006.01)
  (Continued)

(52) U.S. Cl.
  CPC ............ *A61G 7/015* (2013.01); *A61B 5/1115* (2013.01); *A61G 7/018* (2013.01); *A61G 7/0507* (2013.01);
  (Continued)

(58) Field of Classification Search
  CPC ...... A61G 7/015; A61G 7/018; A61G 7/0507; A61G 7/0755; A61G 7/012; A61G 7/005; A61G 7/16; A61G /; A61B 5/1115
  See application file for complete search history.

(56) References Cited

U.S. PATENT DOCUMENTS 3,932,903 A   1/1976   Adams et al.
RE28,754 E   3/1976   Cook et al.
(Continued)

FOREIGN PATENT DOCUMENTS

AU    783695 B2    11/2005
AU    2011232780 A1   4/2012
(Continued)

OTHER PUBLICATIONS

Stryker Medical, "Epic II Critical Care Bed, Model 2030 Operations Manual", 2030-309-001 REV A, Nov. 2007, 53 pages.
(Continued)

*Primary Examiner* — Eric J Kurilla
(74) *Attorney, Agent, or Firm* — Howard & Howard Attorneys PLLC

(57) ABSTRACT

A patient support apparatus comprising a base movable about a floor surface and a deck comprising sections movable between deck configurations including an egress deck configuration. An articulation system coupled to the deck moves the sections. A lift mechanism moves the deck relative to the base between lift configurations including an egress lift configuration. An egress input is arranged for actuation by a user. A bed detection system monitors data associated with the patient support apparatus and communicates with a remote station. A controller interrupts communication of the bed detection system with the remote station, drives the articulation system to move the sections to the egress deck configuration, and drives the lift mecha-
(Continued)

nism to move the support frame to the egress lift configuration in response to actuation of the egress input.

22 Claims, 18 Drawing Sheets

(51) Int. Cl.
    *A61B 5/11*     (2006.01)
    *A61G 7/012*     (2006.01)
    *A61G 7/05*     (2006.01)
    *A61G 7/075*     (2006.01)
    *A61G 7/005*     (2006.01)

(52) U.S. Cl.
    CPC ............ *A61G 7/0755* (2013.01); *A61G 7/005* (2013.01); *A61G 7/012* (2013.01); *A61G 7/0514* (2016.11); *A61G 2203/16* (2013.01)

(56) References Cited

U.S. PATENT DOCUMENTS

| | | | |
|---|---|---|---|
| 4,064,574 A | 12/1977 | Schnitzler |
| 4,175,263 A | 11/1979 | Triplett et al. |
| 4,183,015 A | 1/1980 | Drew et al. |
| 4,242,672 A | 12/1980 | Gault |
| 4,641,387 A | 2/1987 | Bondy et al. |
| 4,691,962 A | 9/1987 | Holdt |
| 4,787,104 A | 11/1988 | Grantham |
| 4,805,249 A | 2/1989 | Usman et al. |
| 4,862,529 A | 9/1989 | Peck |
| 4,959,878 A | 10/1990 | Essek |
| 4,985,946 A | 1/1991 | Foster et al. |
| 5,084,925 A | 2/1992 | Cook |
| 5,134,737 A | 8/1992 | Wyman |
| 5,154,186 A | 10/1992 | Laurin et al. |
| 5,173,975 A | 12/1992 | Peterson |
| 5,230,113 A | 7/1993 | Foster et al. |
| 5,231,721 A | 8/1993 | Fish |
| 5,299,334 A | 4/1994 | Gonzalez |
| 5,354,022 A | 10/1994 | Coonrod |
| 5,398,357 A | 3/1995 | Foster |
| 5,411,044 A | 5/1995 | Andolfi |
| 5,454,126 A | 10/1995 | Foster et al. |
| 5,479,666 A | 1/1996 | Foster et al. |
| 5,526,541 A | 6/1996 | Massey et al. |
| 5,555,582 A | 9/1996 | Jerideau |
| 5,577,279 A | 11/1996 | Foster et al. |
| 5,680,661 A | 10/1997 | Foster et al. |
| 5,708,997 A | 1/1998 | Foster et al. |
| 5,715,548 A * | 2/1998 | Weismiller ............... A61G 7/00 5/611 |
| 5,732,423 A | 3/1998 | Weismiller et al. |
| 5,745,937 A | 5/1998 | Weismiller et al. |
| 5,790,997 A | 8/1998 | Ruehl |
| 5,842,237 A | 12/1998 | Hargest et al. |
| 5,844,488 A | 12/1998 | Musick |
| 5,916,085 A | 6/1999 | Wells |
| 5,933,888 A | 8/1999 | Foster et al. |
| 5,940,910 A | 8/1999 | Weismiller et al. |
| 5,987,673 A | 11/1999 | Smith |
| 6,009,570 A | 1/2000 | Hargest et al. |
| 6,112,345 A | 9/2000 | Foster et al. |
| 6,141,806 A | 11/2000 | Bobey et al. |
| 6,163,903 A | 12/2000 | Weismiller et al. |
| 6,182,310 B1 | 2/2001 | Weismiller et al. |
| 6,240,583 B1 | 6/2001 | Brooke et al. |
| 6,256,822 B1 | 7/2001 | Weston et al. |
| 6,336,235 B1 | 1/2002 | Ruehl |
| 6,427,264 B1 | 8/2002 | Metz et al. |
| 6,430,763 B2 | 8/2002 | Kosumsuppamala et al. |
| 6,453,491 B1 | 9/2002 | Wells et al. |
| 6,539,569 B2 | 4/2003 | O'Connell |
| 6,584,628 B1 | 7/2003 | Kummer et al. |
| 6,629,326 B2 | 10/2003 | Rabe |
| 6,640,360 B2 | 11/2003 | Hornbach et al. |
| 6,694,548 B2 | 2/2004 | Foster et al. |
| 6,701,545 B1 | 3/2004 | Ferneau et al. |
| 6,715,784 B2 | 4/2004 | Koerlin et al. |
| 6,725,474 B2 | 4/2004 | Foster et al. |
| 6,820,293 B2 | 11/2004 | Alverson |
| 6,829,793 B2 | 12/2004 | Brooke et al. |
| 6,928,673 B2 | 8/2005 | Risk, Jr. |
| 6,941,598 B2 | 9/2005 | Ferrand et al. |
| 6,971,132 B2 | 12/2005 | Feinsod |
| 6,978,501 B2 | 12/2005 | Vrzalik |
| 7,000,272 B2 | 2/2006 | Allen et al. |
| 7,058,999 B2 | 6/2006 | Horitani et al. |
| 7,073,219 B2 | 7/2006 | Poulin et al. |
| 7,154,397 B2 | 12/2006 | Zerhusen et al. |
| 7,197,779 B2 | 4/2007 | Shalikar |
| 7,200,882 B2 | 4/2007 | Heimbrock |
| 7,213,279 B2 | 5/2007 | Weismiller et al. |
| 7,251,845 B2 | 8/2007 | Schaller et al. |
| 7,253,366 B2 | 8/2007 | Bhai |
| 7,319,386 B2 | 1/2008 | Collins, Jr. et al. |
| 7,406,731 B2 | 8/2008 | Menkedick et al. |
| 7,415,740 B1 | 8/2008 | Kemper |
| 7,430,770 B2 | 10/2008 | Ramirez |
| 7,458,119 B2 | 12/2008 | Hornbach et al. |
| 7,520,006 B2 | 4/2009 | Menkedick et al. |
| 7,520,009 B1 | 4/2009 | Heck |
| 7,559,101 B2 | 7/2009 | Vrzalik et al. |
| 7,568,247 B2 | 8/2009 | Strobel et al. |
| 7,673,353 B1 | 3/2010 | Khodabandeh |
| 7,690,059 B2 | 4/2010 | Lemire et al. |
| 7,694,368 B2 | 4/2010 | Lewis, Jr. |
| 7,716,762 B2 | 5/2010 | Ferraresi et al. |
| 7,761,939 B2 | 7/2010 | Wiggins et al. |
| 7,761,942 B2 | 7/2010 | Benzo et al. |
| 7,784,128 B2 | 8/2010 | Kramer |
| 7,788,747 B2 | 9/2010 | Kramer et al. |
| 7,788,748 B2 | 9/2010 | Wurdeman |
| 7,805,782 B2 | 10/2010 | Hakamiun et al. |
| 7,845,034 B2 | 12/2010 | Kim |
| 7,886,379 B2 | 2/2011 | Benzo et al. |
| 7,905,242 B2 | 3/2011 | Kline |
| 7,917,978 B2 | 4/2011 | Ruschke et al. |
| 8,042,206 B2 | 10/2011 | Genaro |
| 8,065,764 B2 | 11/2011 | Kramer |
| 8,104,118 B2 | 1/2012 | Derenne et al. |
| RE43,155 E | 2/2012 | Allen et al. |
| RE43,193 E * | 2/2012 | Osborne ............... A61B 5/1115 5/618 |
| 8,127,380 B2 | 3/2012 | Wurdeman |
| 8,156,586 B2 | 4/2012 | Reed et al. |
| RE43,532 E | 7/2012 | Menkedick et al. |
| 8,239,983 B2 | 8/2012 | Chinn |
| 8,272,087 B2 | 9/2012 | Westermann |
| 8,296,884 B2 | 10/2012 | Heimbrock |
| 8,334,779 B2 | 12/2012 | Zerhusen et al. |
| 8,336,133 B2 | 12/2012 | Palay et al. |
| 8,336,134 B2 | 12/2012 | Jelinek |
| 8,341,779 B2 | 1/2013 | Hornbach et al. |
| 8,353,071 B2 | 1/2013 | Turner et al. |
| 8,413,270 B2 | 4/2013 | Turner et al. |
| 8,413,273 B2 | 4/2013 | Hornbach et al. |
| 8,413,274 B2 | 4/2013 | Weismiller et al. |
| 8,453,283 B2 | 6/2013 | O'Keefe |
| 8,474,072 B2 | 7/2013 | O'Keefe et al. |
| 8,474,921 B2 | 7/2013 | Newkirk et al. |
| 8,495,774 B2 | 7/2013 | Soltani |
| 8,516,637 B2 | 8/2013 | Karwal et al. |
| 8,522,379 B2 | 9/2013 | Turner |
| 8,578,531 B2 | 11/2013 | Abernathey et al. |
| 8,631,524 B2 | 1/2014 | Derenne et al. |
| 8,640,285 B2 | 2/2014 | Heimbrock et al. |
| 8,646,124 B2 | 2/2014 | Stryker et al. |
| 8,677,535 B2 | 3/2014 | Turner |
| 8,689,376 B2 | 4/2014 | Becker et al. |
| 8,713,727 B2 | 5/2014 | Heimbrock et al. |
| 8,732,875 B2 | 5/2014 | O'Keefe |
| 8,745,786 B2 | 6/2014 | Andrienko et al. |
| 8,756,735 B2 | 6/2014 | Heimbrock et al. |

(56) References Cited

U.S. PATENT DOCUMENTS

| | | |
|---|---|---|
| 8,793,824 B2 | 8/2014 | Poulos et al. |
| 8,826,475 B2 | 9/2014 | Jackson |
| 8,844,075 B2 | 9/2014 | Heimbrock |
| 8,844,078 B2 | 9/2014 | Hornbach et al. |
| 8,863,331 B2 | 10/2014 | Valentino et al. |
| 8,887,329 B2 | 11/2014 | Soltani |
| 8,910,329 B2 | 12/2014 | Turner et al. |
| 8,959,680 B2 | 2/2015 | Tesar et al. |
| 8,959,681 B2 | 2/2015 | Richards |
| 8,973,186 B2 | 3/2015 | Bhai |
| 8,973,187 B2 | 3/2015 | Hornbach |
| 9,013,313 B2 | 4/2015 | Paine |
| 9,038,214 B2 | 5/2015 | Hardin |
| 9,079,089 B2 | 7/2015 | Lokken et al. |
| 9,125,758 B2 | 9/2015 | Skreosen |
| 9,125,785 B2 | 9/2015 | Trees |
| 9,138,173 B2 | 9/2015 | Penninger et al. |
| 9,149,403 B2 | 10/2015 | Turner et al. |
| 9,173,797 B2 | 11/2015 | Andrienko |
| 9,179,863 B2 | 11/2015 | Brauers et al. |
| 9,216,123 B2 | 12/2015 | Tekulve |
| 9,228,885 B2* | 1/2016 | Zerhusen ............ A61G 7/0527 |
| 9,253,891 B2 | 2/2016 | Williams |
| 9,265,677 B2 | 2/2016 | Manouchehri et al. |
| 9,277,827 B2 | 3/2016 | Hornbach et al. |
| 9,329,076 B2 | 5/2016 | Meyer et al. |
| 9,552,714 B2 | 1/2017 | Ribble et al. |
| 9,978,244 B2 | 5/2018 | Ribble et al. |
| 2003/0167568 A1 | 9/2003 | Brooke |
| 2004/0019967 A1 | 2/2004 | Gant |
| 2004/0074414 A1 | 4/2004 | Phillips |
| 2004/0158923 A1 | 8/2004 | Perez et al. |
| 2005/0011006 A1 | 1/2005 | Ellen et al. |
| 2005/0235418 A1 | 10/2005 | Jacques et al. |
| 2006/0053555 A1 | 3/2006 | Poulos et al. |
| 2006/0075558 A1* | 4/2006 | Lambarth ............ A61G 1/0293 5/611 |
| 2006/0085914 A1 | 4/2006 | Peterson et al. |
| 2006/0117484 A1* | 6/2006 | Derenne ............ A61G 13/12 5/624 |
| 2006/0117485 A1* | 6/2006 | Brophy ............ A61G 13/12 5/624 |
| 2006/0225215 A1* | 10/2006 | Krecow ............ A61G 13/12 5/649 |
| 2007/0038155 A1 | 2/2007 | Kelly et al. |
| 2007/0089238 A1 | 4/2007 | Kramer et al. |
| 2007/0124859 A1* | 6/2007 | Stryker ............ A61G 7/1046 5/81.1 R |
| 2007/0169269 A1 | 7/2007 | Wells |
| 2009/0044334 A1 | 2/2009 | Parsell et al. |
| 2009/0094745 A1 | 4/2009 | Benzo et al. |
| 2009/0126114 A1 | 5/2009 | Kral et al. |
| 2009/0188042 A1* | 7/2009 | Derenne ............ A61G 7/0521 5/430 |
| 2010/0005592 A1 | 1/2010 | Poulos et al. |
| 2010/0017964 A1 | 1/2010 | Kruse |
| 2010/0064439 A1 | 3/2010 | Soltani |
| 2010/0170041 A1 | 7/2010 | Heimbrock et al. |
| 2010/0212087 A1 | 8/2010 | Leib et al. |
| 2010/0229299 A1 | 9/2010 | Lear |
| 2011/0068932 A1 | 3/2011 | Flocard et al. |
| 2011/0314602 A1 | 12/2011 | Stryker et al. |
| 2012/0023670 A1 | 2/2012 | Zerhusen et al. |
| 2012/0047655 A1* | 3/2012 | O'Keefe ............ A61G 7/018 5/610 |
| 2012/0096644 A1 | 4/2012 | Heimbrock |
| 2012/0110741 A1 | 5/2012 | Mears et al. |
| 2012/0117730 A1* | 5/2012 | Lemire ............ A61G 5/10 5/611 |
| 2012/0117732 A1 | 5/2012 | O'Keefe |
| 2012/0124745 A1 | 5/2012 | Heimbrock et al. |
| 2012/0124746 A1 | 5/2012 | Andrienko et al. |
| 2012/0137439 A1 | 6/2012 | Heimbrock |
| 2012/0137440 A1 | 6/2012 | Richards |
| 2012/0144588 A1 | 6/2012 | Heimbrock et al. |
| 2012/0198626 A1 | 8/2012 | Richards |
| 2012/0198628 A1 | 8/2012 | Richards |
| 2012/0204351 A1 | 8/2012 | Revenus et al. |
| 2012/0246830 A1 | 10/2012 | Hornbach |
| 2013/0086746 A1 | 4/2013 | Vanderpohl |
| 2013/0125310 A1 | 5/2013 | Manouchehri |
| 2013/0212807 A1 | 8/2013 | Manson et al. |
| 2013/0227787 A1* | 9/2013 | Herbst ............ A61G 7/0509 5/611 |
| 2013/0340168 A1* | 12/2013 | Meyer ............ A61G 7/0506 5/615 |
| 2014/0076644 A1* | 3/2014 | Derenne ............ A61G 7/012 180/19.2 |
| 2014/0265497 A1 | 9/2014 | Hough et al. |
| 2014/0313030 A1 | 10/2014 | Ten Kate et al. |
| 2014/0331410 A1 | 11/2014 | Heimbrock et al. |
| 2014/0333440 A1 | 11/2014 | Kiani |
| 2014/0343889 A1 | 11/2014 | Ben Shalom et al. |
| 2015/0135440 A1 | 5/2015 | Chiacchira et al. |
| 2015/0164722 A1 | 6/2015 | Roussy et al. |
| 2015/0182400 A1* | 7/2015 | Meyer ............ A61G 7/05715 5/710 |
| 2015/0231010 A1 | 8/2015 | Nilsson et al. |
| 2015/0238123 A1 | 8/2015 | Yakam et al. |
| 2015/0257952 A1 | 9/2015 | Zerhusen et al. |
| 2015/0297432 A1 | 10/2015 | Poulos et al. |
| 2015/0305955 A1 | 10/2015 | Simmonds et al. |
| 2015/0320625 A1 | 11/2015 | White |
| 2016/0022039 A1 | 1/2016 | Paul et al. |
| 2016/0120717 A1 | 5/2016 | Wurdeman |
| 2016/0140307 A1* | 5/2016 | Brosnan ............ G16H 40/67 600/324 |
| 2016/0193095 A1 | 7/2016 | Roussy et al. |
| 2016/0213538 A1 | 7/2016 | Lus |
| 2016/0302985 A1 | 10/2016 | Tessmer et al. |
| 2016/0310336 A1 | 10/2016 | Ertelt |
| 2016/0310340 A1 | 10/2016 | Heidingsfelder-Bongard et al. |
| 2016/0367420 A1 | 12/2016 | Zerhusen et al. |
| 2017/0027789 A1* | 2/2017 | St.John ............ A61G 7/0506 |
| 2017/0056262 A1 | 3/2017 | Yamada et al. |
| 2017/0124844 A1 | 5/2017 | Huster et al. |
| 2017/0128295 A1 | 5/2017 | Tekulve |
| 2017/0172829 A1* | 6/2017 | Tessmer ............ A61G 7/0509 |
| 2017/0281438 A1 | 10/2017 | Elku et al. |
| 2018/0000673 A1 | 1/2018 | Bartley |
| 2018/0116885 A1 | 5/2018 | St. John et al. |

FOREIGN PATENT DOCUMENTS

| | | |
|---|---|---|
| CA | 2018815 C | 11/1999 |
| CA | 2293085 A1 | 6/2001 |
| CA | 2696686 C | 1/2015 |
| CN | 101077325 A | 11/2007 |
| CN | 201905562 U | 7/2011 |
| CN | 202843982 U | 4/2013 |
| CN | 101868215 B | 8/2013 |
| CN | 204192905 U | 3/2015 |
| CN | 204379588 U | 6/2015 |
| CN | 204814540 U | 12/2015 |
| DE | 2749146 A1 | 5/1978 |
| DE | 4039253 A1 | 6/1992 |
| DE | 19634419 A1 | 3/1998 |
| DE | 202004003299 U1 | 5/2004 |
| EP | 0375206 B1 | 3/1994 |
| EP | 0746298 B1 | 3/2003 |
| EP | 0932385 B1 | 3/2004 |
| EP | 0957877 B1 | 4/2005 |
| EP | 1545345 A1 | 6/2005 |
| EP | 1789278 A2 | 5/2007 |
| EP | 1416897 B1 | 5/2008 |
| EP | 1487392 B1 | 5/2008 |
| EP | 1459722 B1 | 6/2010 |
| EP | 1976433 B1 | 3/2011 |
| EP | 2484326 A2 | 8/2012 |
| EP | 2484326 A3 | 12/2012 |
| EP | 1693037 B1 | 1/2013 |
| EP | 1948109 A4 | 4/2013 |

(56) References Cited

FOREIGN PATENT DOCUMENTS

| | | |
|---|---|---|
| EP | 2174670 B1 | 4/2013 |
| EP | 2174631 B1 | 6/2013 |
| EP | 2462911 A3 | 9/2013 |
| EP | 2275071 B1 | 11/2013 |
| EP | 2151222 B1 | 3/2014 |
| EP | 2716269 A1 | 4/2014 |
| EP | 2462912 B1 | 11/2014 |
| EP | 2863858 A4 | 10/2015 |
| EP | 1916926 B1 | 11/2015 |
| EP | 2481388 B1 | 11/2015 |
| EP | 2327385 B1 | 3/2016 |
| EP | 2854602 B1 | 9/2016 |
| GB | 905708 A | 9/1962 |
| GB | 1212107 A | 11/1970 |
| GB | 2185883 A | 8/1987 |
| JP | H03151913 A | 6/1991 |
| JP | H04341264 A | 11/1992 |
| JP | H0731644 A | 2/1995 |
| JP | H11104190 A | 4/1999 |
| JP | 2002095703 A | 4/2002 |
| JP | 2005066250 A | 3/2005 |
| JP | 4854665 B2 | 1/2012 |
| JP | 2013240601 A | 12/2013 |
| JP | 2014188340 A | 10/2014 |
| JP | 2015107283 A | 6/2015 |
| KR | 20130076922 A | 7/2013 |
| KR | 20130111088 A | 10/2013 |
| TW | 201316976 A | 5/2013 |
| WO | 9219203 A1 | 11/1992 |
| WO | 9520933 A1 | 8/1995 |
| WO | 1998007402 A1 | 2/1998 |
| WO | 2004014193 A1 | 2/2004 |
| WO | 2006023447 A2 | 3/2006 |
| WO | 2006056146 A1 | 6/2006 |
| WO | WO2006138252 A2 | 12/2006 |
| WO | 2007055051 A1 | 5/2007 |
| WO | 2007145544 A1 | 12/2007 |
| WO | 2008130741 A2 | 10/2008 |
| WO | 2009029996 A1 | 3/2009 |
| WO | 2011113070 A1 | 9/2011 |
| WO | 2013192411 A2 | 12/2013 |
| WO | 2014029988 A1 | 2/2014 |
| WO | 2015126742 A1 | 8/2015 |
| WO | 2016171746 A1 | 10/2016 |

OTHER PUBLICATIONS

Astral Healthcare, "DOC Classic Opthalmology Day Surgery Chair Webpage and Video", 2017, 6 pages.
English language abstract and machine-assisted English translation for JPH 04-341264 extracted from espacenet.com database on Jan. 2, 2019, 9 pages.
English language abstract and machine-assisted English translation for CN 101077325 extracted from espacenet.com database on Oct. 24, 2018, 7 pages.
English language abstract and machine-assisted English translation for CN 201905562 extracted from espacenet.com database on Oct. 24, 2018, 8 pages.
English language abstract and machine-assisted English translation for CN 202843982 extracted from espacenet.com database on Oct. 24, 2018, 7 pages.
English language abstract and machine-assisted English translation for CN 204192905 extracted from espacenet.com database on Oct. 24, 2018, 8 pages.
English language abstract and machine-assisted English translation for CN 204814540 extracted from espacenet.com database on Jan. 2, 2019, 10 pages.
English language abstract and machine-assisted English translation for CN204379588 extracted from espacenet.com database on Oct. 24, 2018, 8 pages.
English language abstract and machine-assisted English translation for DE 196 34 419 extracted from espacenet.com database on Oct. 24, 2018, 6 pages.
English language abstract and machine-assisted English translation for DE 20 2004 003 299 extracted from espacenet.com database on Jan. 2, 2019, 8 pages.
English language abstract and machine-assisted English translation for DE 27 49 146 extracted from espacenet.com database on Oct. 24, 2018, 17 pages.
English language abstract and machine-assisted English translation for DE 40 39 253 extracted from espacenet.com database on Oct. 24, 2018, 7 pages.
English language abstract and machine-assisted English translation for JP 2002-095703 extracted from espacenet.com database on Oct. 24, 2018, 12 pages.
English language abstract and machine-assisted English translation for JP 2005-066250 extracted from espacenet.com database on Jan. 2, 2019, 9 pages.
English language abstract and machine-assisted English translation for JP 2014-188340 extracted from espacenet.com database on Oct. 24, 2018, 10 pages.
English language abstract and machine-assisted English translation for JP 2015-107283 extracted from espacenet.com database on Oct. 24, 2018, 19 pages.
English language abstract and machine-assisted English translation for JPH 03-151913 extracted from espacenet.com database on Jan. 2, 2019, 5 pages.
English language abstract and machine-assisted English translation for JPH 07-31644 extracted from espacenet.com database on Oct. 24, 2018, 6 pages.
English language abstract and machine-assisted English translation for JPH 11-104190 extracted from espacenet.com database on Jan. 2, 2019, 15 pages.
English language abstract and machine-assisted English translation for KR 2013-0076922 extracted from espacenet.com database on Oct. 24, 2018, 8 pages.
English language abstract and machine-assisted English translation for KR 2013-0111088 extracted from espacenet.com database on Oct. 24, 2018, 11 pages.
English language abstract and machine-assisted English translation for TW 201316976 extracted from espacenet.com database on Jan. 2, 2019, 12 pages.
English language abstract for CN 101868215 extracted from espacenet.com database on Oct. 24, 2018, 2 pages.
English language abstract for JP 2013-240601 extracted from espacenet.com database on Oct. 24, 2018, 2 pages.
English language abstract for WO 2007/055051 and machine-assisted English translation for corresponding JP 2007-130055 extracted from espacenet.com database on Jan. 2, 2019, 17 pages.
Ford Motor Company, "Memory Seat Escape Video", https://www.youtube.com/watch?v=xlghNmAK-7A, 2013, 2 pages.
Hill-Rom, "Centrella Smart+Bed Brochure" 2017, 11 pages.
Hill-Rom, "Centrella Smart+Bed Therapeutic Surfaces Brochure", Sep. 20, 2017, 3 pages.
Hill-Rom, "The Hill-Rom 900 Accella Bed Brochure", May 12, 2017, 16 pages.
Machine-assisted English translation for JP 4854665 extracted from espacenet.com database on Jan. 2, 2019, 31 pages.
Supportec Trade, "Surgery Chairs-Classic and Maxi Webpages", https://supportec-trade.nl/ formerly http://www.dogemedical.com/pages/en/products/surgery-chairs/doc-classic.php, 2017, 10 pages.
Ultracomfort America Furniture Manufacturing, "UltraComfort Stellar UC550 Large Lift Chair Webpage and Video", https://www.recliners.la/products/ultra-comfort-stellar-550-large-lift-chair, 2018, 3 pages.
U.S. Appl. No. 16/020,085, filed Jun. 27, 2018.
U.S. Appl. No. 16/134,048, filed Sep. 18, 2018.
U.S. Appl. No. 16/134,438, filed Sep. 18, 2018.
InkBed, "Brand New Model InkBed Patened Fully Adjustable Tattoo Table & Bed Webpage", http://www.inkbed.com/brand-new-model-inkbed-patented-fully-adjustable-tattoo-table-bed/, 2019, 3 pages.

* cited by examiner

PATENT SUPPORT APPARATUS FOR CONTROLLING PATIENT INGRESS AND EGRESS

CROSS-REFERENCE TO RELATED APPLICATION

The subject patent application claims priority to and all the benefits of U.S. Provisional Patent Application No. 62/560,407 filed on Sep. 19, 2017, the disclosure of which is hereby incorporated by reference in its entirety.

TECHNICAL FIELD

The present disclosure relates, generally, to patient support apparatuses and, more specifically, to a patient support apparatus for controlling patient ingress and egress.

BACKGROUND

Patient support apparatuses, such as hospital beds, stretchers, cots, tables, wheelchairs, and chairs are used to help caregivers facilitate care of patients in a health care setting. Conventional patient support apparatuses comprise a base, a support frame, a patient support deck operatively attached to the support frame, a lift assembly for lifting and lowering the support frame relative to the base, and actuators arranged to move sections of the patient support deck relative to the support frame.

Certain conventional patient support apparatuses, such as those realized as hospital beds, are primarily employed to provide support to a patient lying on the patient support deck. To this end, one or more sections of the patient support deck provide support to the patient's head, torso, legs, and feet, allowing the patient to lay on their side, on their back in a supine position, and the like. In addition, one or more sections of the patient support deck can typically be moved or oriented relative to one another to promote patient comfort and to help facilitate patient mobility. By way of example, the patient support deck may be movable into a fowlers position to allow the patient to lay upright.

In order to allow the patient to exit the hospital bed, the caregiver generally activates the lift assembly to lower the patient support deck towards the base so as to position the patient vertically near the floor. Depending on the type of patient support apparatus, the caregiver may also have to disarm or otherwise interrupt certain patient monitoring devices, such as bed exit systems adapted to alert caregivers when the patient attempts to exit the patient support apparatus without assistance. While the patient can generally still exit the patient support apparatus even if the bed exit system is armed, the alarm will still sound if the caregiver forgets to disable the bed exit system before helping the patient exit the patient support apparatus.

Once the bed exit systems have been disarmed, the patient re-orients their body to bring their legs and feet into contact with the floor at one side of the patient support apparatus. To this end, the patient typically sits upright and turns sideways while moving their legs and feet away from the patient support deck to bring their feet into contact with the floor to stand. Upon returning to the patient support apparatus, the patient generally follows the same procedure in reverse by sitting upright on the patient support apparatus with their feet on the floor surface, and then subsequently swinging their legs back onto the patient support apparatus. However, depending on where the patient sits when entering the patient support apparatus, their body may be too far towards a head-end or a foot-end. In such circumstances, a caregiver generally has to help reposition the patient to ensure proper support.

While conventional patient support apparatuses have generally performed well for their intended purpose, there remains a need in the art for a patient support apparatus which overcomes the disadvantages in the prior art while, at the same time, contributing to improved patient mobility, safety, and ambulation.

DETAILED DESCRIPTION OF THE EMBODIMENTS

Figure 1:
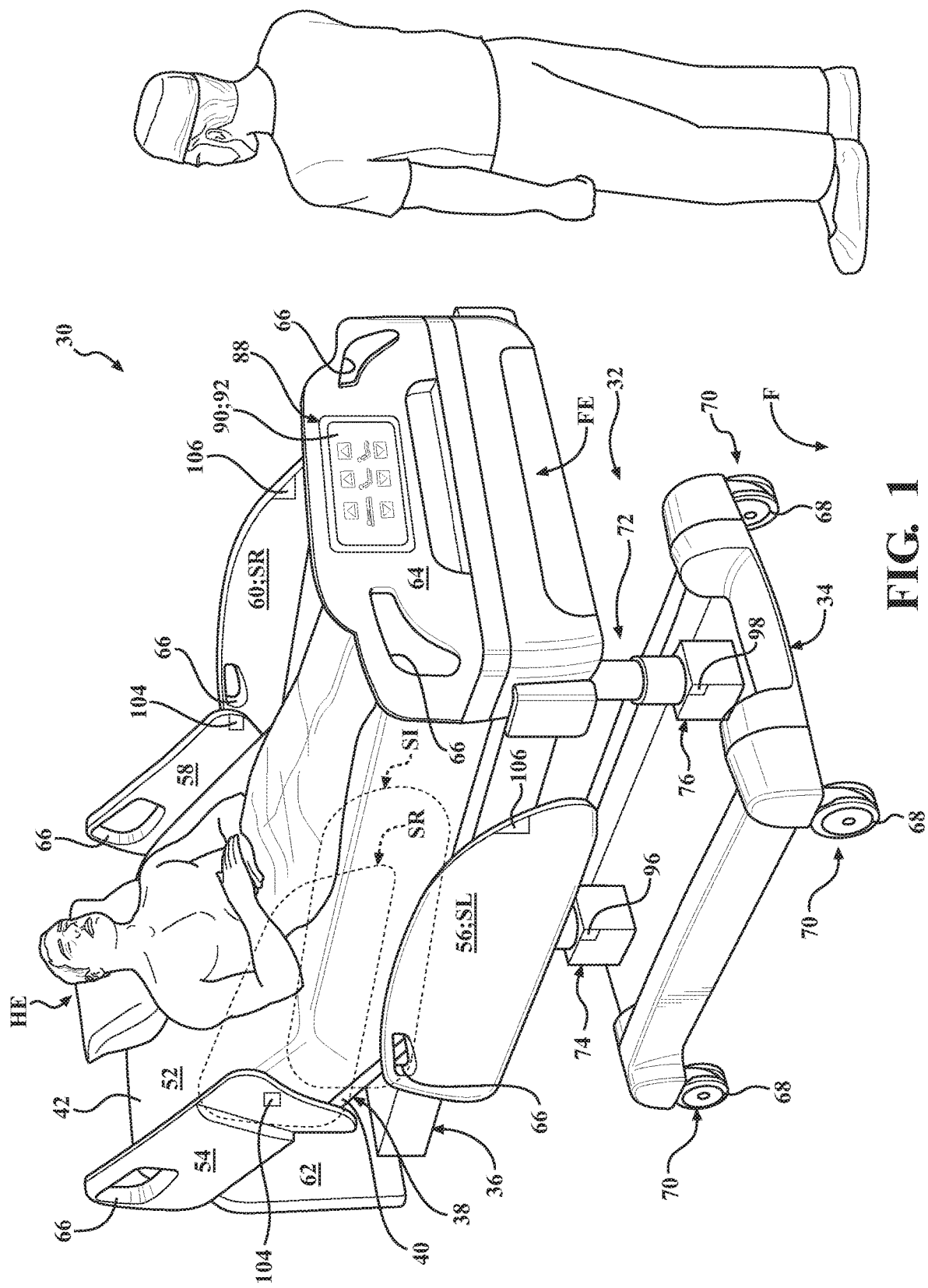
FIG. 1 is perspective view of a patient support apparatus.

Referring to FIGS. 1-8, a patient support apparatus 30 is shown for supporting a patient in a health care setting. The patient support apparatus 30 illustrated throughout the drawings is realized as a hospital bed. In other embodiments, however, the patient support apparatus 30 may be a stretcher, a cot, a table, a wheelchair, a chair, or a similar apparatus utilized in the care of a patient.

A support structure 32 provides support for the patient. In the representative embodiment illustrated herein, the support structure 32 comprises a base 34 movable about a floor surface F, an intermediate frame 36, and a patient support deck 38. The intermediate frame 36 and the patient support deck 38 are spaced above the base 34 in FIG. 1. As is described in greater detail below, the intermediate frame 36 and the patient support deck 38 are arranged for movement relative to the base 34.

As is best depicted in FIGS. 3-8, the patient support deck 38 has at least one deck section 40 arranged for movement relative to the intermediate frame 36 to support the patient in different positions, orientations, and the like. The deck sections 40 of the patient support deck 38 provide a patient support surface 42 upon which the patient is supported. More specifically, in the representative embodiment of the patient support apparatus 30 illustrated herein, the patient support deck 38 has four deck sections 40 which cooperate to define the patient support surface 42: a back section 44, a seat section 46, a leg section 48, and a foot section 50. Here, the seat section 46 is fixed to the intermediate frame 36 and is not arranged for movement relative thereto. However, it will be appreciated that the seat section 46 could be movable relative to other deck sections 40 in some embodiments. Conversely, the back section 44 and the leg section 48 are arranged for movement relative to each other and to the intermediate frame 36, as described in greater detail below, and the foot section 50 is arranged to move partially concurrently with the leg section 48. Other configurations and arrangements are contemplated.

A mattress 52 is disposed on the patient support deck 38 during use. The mattress 52 comprises a secondary patient support surface upon which the patient is supported. The base 34, the intermediate frame 36, and the patient support deck 38 each have a head-end HE and a foot-end FE corresponding to designated placement of the patient's head and feet on the patient support apparatus 30. It will be appreciated that the specific configuration of the support structure 32 may take on any known or conventional design, and is not limited to that specifically illustrated and described herein. In addition, the mattress 52 may be omitted in certain embodiments, such that the patient can rest directly on the patient support surface 42 defined by the deck sections 40 of the patient support deck 38.

Side rails 54, 56, 58, 60 are coupled to the support structure 32 and are supported by the intermediate frame 36. A first side rail 54 is positioned at a right head-end of the intermediate frame 36. A second side rail 56 is positioned at a right foot-end of the intermediate frame 36. A third side rail 58 is positioned at a left head-end of the intermediate frame 36. A fourth side rail 60 is positioned at a left foot-end of the intermediate frame 36. As is described in greater detail below in connection with FIGS. 9-18, one or more of the side rails 54, 56, 58, 60 are advantageously movable between a raised position SR in which they block ingress and egress into and out of the patient support apparatus 30, one or more intermediate positions SI, and a lowered position SL in which they are not an obstacle to such ingress and egress. The side rails 54, 56, 58, 60 may be manually movable between the positions SR, SI, SL, such as with a mechanical linkage, or may be provided with actuators to assist the caregiver in moving between the positions SR, SI, SL. The Applicant has described embodiments of patient support apparatuses having side rails equipped with actuators for "motorized" movement in United States Patent Application Publication No. US 2017/0172829 A1, the disclosure of which is hereby incorporated by reference in its entirety. Other configurations are contemplated.

The side rails 54, 56, 58, 60 could be of any suitable type, arrangement, or configuration sufficient to selectively limit patient ingress/egress from the patient support apparatus 30. It will be appreciated that there may be fewer side rails for certain embodiments, such as where the patient support apparatus 30 is realized as a stretcher or a cot. Moreover, it will be appreciated that in certain configurations, the patient support apparatus 30 may not include any side rails. Similarly, it will be appreciated that side rails may be attached to any suitable component or structure of the patient support apparatus 30. Furthermore, in certain embodiments the side rails are coupled to one of the deck sections 40 for concurrent movement. In FIGS. 3-7, which each depict right-side views of the patient support apparatus 30, the side rails are omitted for clarity.

As shown in FIGS. 1 and 3-8, a headboard 62 and a footboard 64 are coupled to the intermediate frame 36 of the support structure 32. However, it will be appreciated that the headboard 62 and/or footboard 64 may be coupled to other locations on the patient support apparatus 30, such as the base 34, or may be omitted in certain embodiments.

One or more grips 66 (or "handles") are shown in FIG. 1 as being integrated into the side rails 54, 56, 58, 60, the headboard 62, and the footboard 64. As is described in greater detail below, the grips 66 formed in the side rails 54, 56, 58, 60 are arranged to help facilitate patient egress from the patient support apparatus 30. It will be appreciated that the grips 66 formed in the side rails 54, 56, 58, 60, as well as the grips 66 formed in the headboard 62 and the footboard 64, can also be used by a caregiver to facilitate movement of the patient support apparatus 30 over floor surfaces. Additional grips 66 may be integrated into other components of the patient support apparatus 30, such as the intermediate frame 36. The grips 66 are shaped so as to be grasped by the patient or the caregiver. It will be appreciated that the grips 66 could be integrated with or operatively attached to any suitable portion of the patient support apparatus 30, or may be omitted from certain parts of the patient support apparatus 30 in certain embodiments.

Wheels 68 are coupled to the base 34 to facilitate transportation over floor surfaces F. The wheels 68 are arranged in each of four quadrants of the base 34, adjacent to corners of the base 34. In the embodiment shown in FIG. 1, the wheels 68 are caster wheels able to rotate and swivel relative to the support structure 32 during transport. Here, each of the wheels 68 forms part of a caster assembly 70 mounted to the base 34. It should be understood that various configurations of the caster assemblies 70 are contemplated. In addition, in some embodiments, the wheels 68 are not caster wheels. Moreover, it will be appreciated that the wheels 68 may be non-steerable, steerable, non-powered, powered, or combinations thereof. While the representative embodiment of the patient support apparatus 30 illustrated herein employs four wheels 68, additional wheels are also contemplated. For example, the patient support apparatus 30 may comprise four non-powered, non-steerable wheels, along with one or more additional powered wheels. In some cases, the patient support apparatus 30 may not include any wheels. In other embodiments, one or more auxiliary wheels (powered or non-powered), which are optionally movable between stowed positions and deployed positions, may be coupled to the support structure 32. In some cases, when auxiliary wheels are located between caster assemblies 70 and contact the floor surface in the deployed position, they cause two of the caster assemblies 70 to be lifted off the floor surface, thereby shortening a wheel base of the patient support apparatus 30. A fifth wheel may also be arranged substantially in a center of the base 34.

The patient support apparatus 30 further comprises a lift mechanism, generally indicated at 72, which operates to lift and lower the intermediate frame 36 relative to the base 34 which, in turn, moves the patient support deck 38 relative to the base 34 between a plurality of lift configurations, including a raised lift configuration 72A where the patient support deck 38 is elevated vertically above the base 34 (see FIGS. 3-4), a lowered lift configuration 72B where the patient support deck 38 is positioned adjacent to the base 34 (see FIGS. 5-6), or any desired vertical position therebetween. To this end, the lift mechanism 72 comprises a head-end lift actuator 74 and a foot-end lift actuator 76 which are each arranged to facilitate movement of the intermediate frame 36 with respect to the base 34. More specifically, the head-end lift actuator 74 is configured to move the head-end HE of the intermediate frame 36 relative to the base 34 between a raised head-end position 74A (see FIGS. 3-4), a lowered head-end position 74B (see FIGS. 5-6), and to other positions therebetween. Similarly, the foot-end lift actuator 76 is configured to move the foot-end FE of the intermediate frame 36 relative to the base 34 between a raised foot-end position 76A (see FIGS. 3-4), a lowered foot-end position 76B (see FIGS. 5-6), and to other positions therebetween.

The lift actuators 74, 76 may be realized as linear actuators, rotary actuators, or other types of actuators, and may be electrically, hydraulically, and/or pneumatically operated or combinations thereof. It is contemplated that, in some embodiments, different arrangements of lift actuators may be employed, such as with rotary actuators coupled to the base 34 and to the intermediate frame 36 with a linkage extending therebetween. The construction of the lift mechanism 72, the head-end lift actuator 74, and/or the foot-end lift actuator 76 may take on any known or conventional design, and is not limited to that specifically illustrated. By way of non-limiting example, the lift mechanism 72 could comprise a "scissor" linkage arranged between the base 34 and the intermediate frame 36 with one or more actuators configured to facilitate vertical movement of the patient support deck 38.

Figure 5:
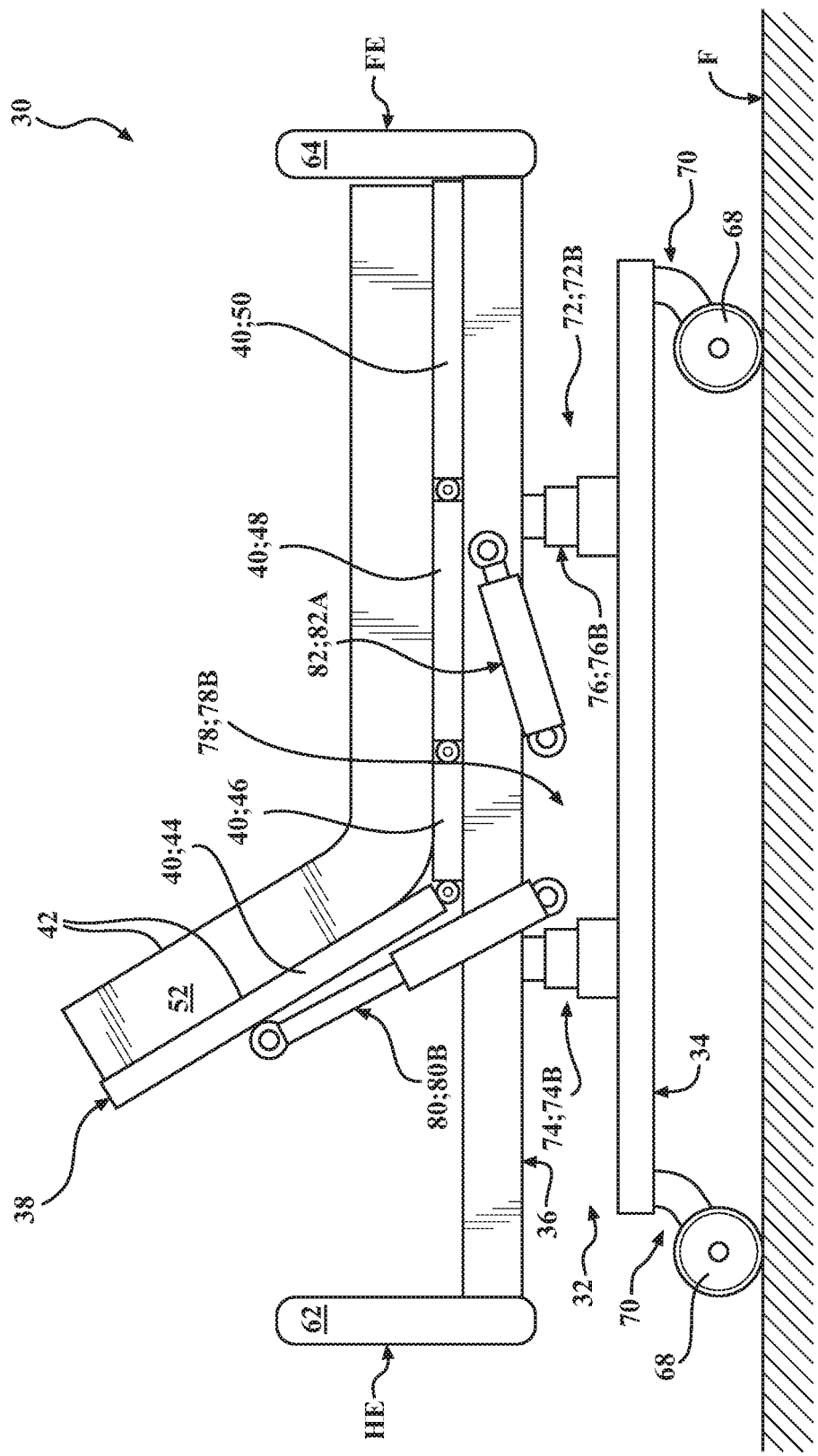
FIG. 5 is another right-side view of the patient support apparatus of FIGS. 3-4, shown with the lift mechanism supporting the patient support deck in a second vertical configuration adjacent to the base, and shown with the patient support deck arranged to support the patient in the fowlers position.
Figure 6:
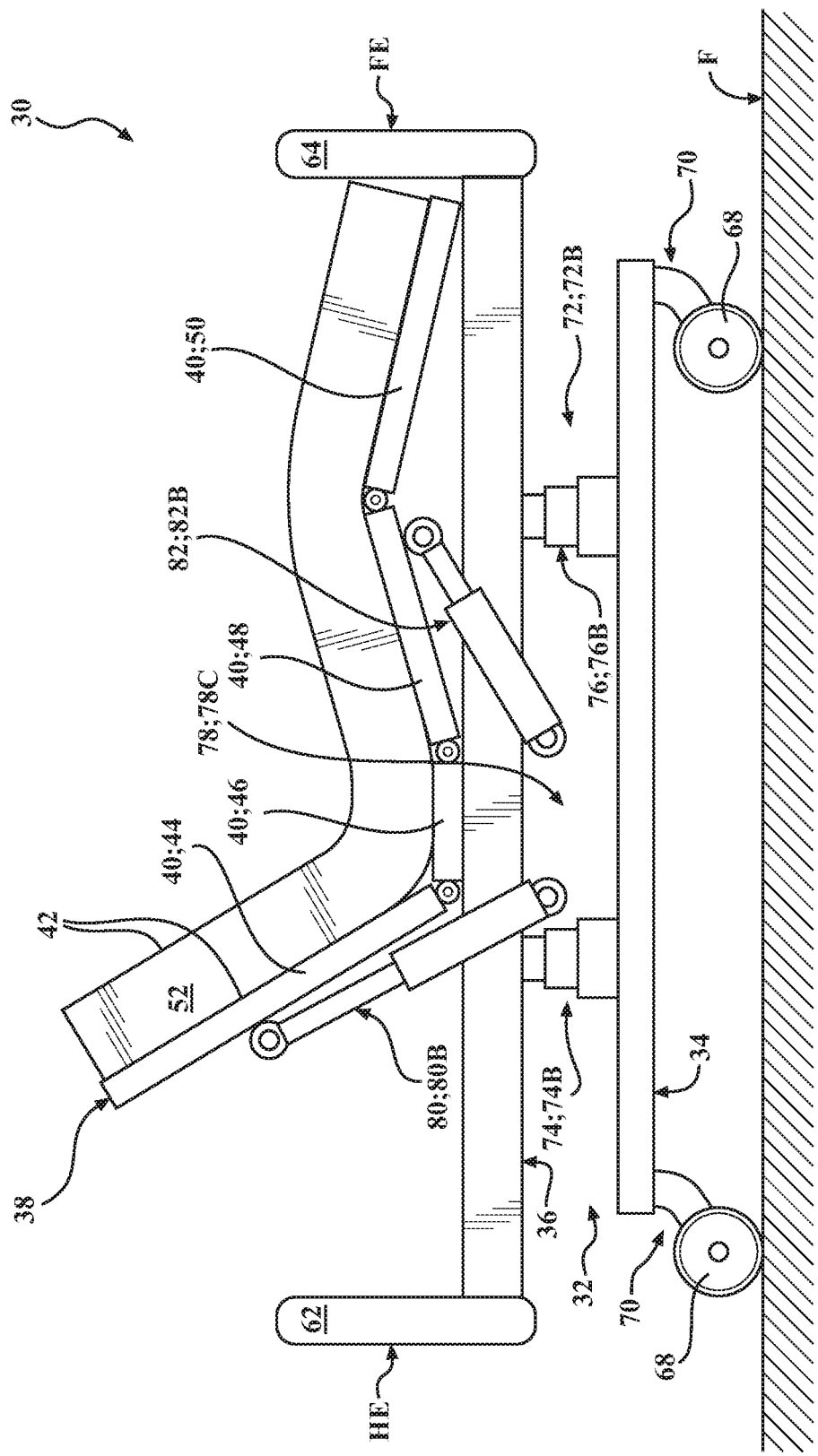
FIG. 6 is another right-side view of the patient support apparatus of FIGS. 3-5, shown with the lift mechanism supporting the patient support deck in the second vertical configuration adjacent to the base, and shown with the patient support deck arranged to support the patient in a modified fowlers position.

As is described in greater detail below, the lift mechanism 72 is also configured to move the patient support deck 38 relative to the base 34 to an egress lift configuration 72C (see FIGS. 7-8). Here, the egress lift configuration 72C is defined with at least a portion of the patient support deck 38 arranged vertically higher than the lowered lift configuration 72B which is depicted in FIGS. 5-6.

Those having ordinary skill in the art will appreciate that, depending on the specific configuration of the patient support apparatus 30, as well as the physical characteristics of the patient, positioning the lift mechanism 72 in the lowered lift configuration 72B (see FIGS. 5-6) may place the patient support surface 42 too close to the floor surface F to facilitate proper ambulation away from the patient support apparatus 30. Put differently, patient ambulation may be better achieved in a slightly raised lift configuration where the patient can transition from sitting to standing without excessive effort. In some embodiments, such as the embodiment illustrated in FIGS. 7-8, the egress lift configuration 72C is defined by the head-end lift actuator 74 being in an egress head-end position 74C and the foot-end lift actuator 76 being in an egress foot-end position 76C. Here, the egress head-end position 74C is vertically higher than the lowered head-end position 74B (compare FIGS. 7-8 to FIGS. 5-6), and is vertically higher than the egress foot-end position 76C so as to place the patient support deck 38 in a slight reverse Trendelenburg configuration. Other arrangement and configurations are contemplated, and the egress lift configuration 72C, the egress head-end position 74C, and the egress foot-end position 76C will each be described in greater detail below.

As noted above, the patient support deck 38 is operatively attached to the intermediate frame 36, and the deck sections 40 are arranged for movement relative to the intermediate frame 36. In the representative embodiment illustrated herein, the patient support apparatus 30 comprises an articulation system, generally indicated at 78, coupled to the patient support deck 38 to move the deck sections 40 relative to one another. To this end, the articulation system 78 comprises a back deck actuator 80 to move the back section 44 between a plurality of back rest configurations, including a back flat configuration 80A (see FIG. 3) and a back egress configuration 80B (see FIGS. 4-8). The articulation system 78 also comprises a leg deck actuator 82 to move the leg section 48 between a plurality of leg rest configurations, including a leg flat configuration 82A (see FIGS. 3-5), a leg egress configuration 82B (see FIGS. 6-7), and a leg ingress configuration 82C (see FIG. 8). As is described in greater detail below, leg ingress configuration 82C is employed to facilitate patient ingress, and the back egress configuration 80B and the leg egress configuration 82B are employed to help facilitate patient egress.

It will be appreciated that these configurations 80B, 82B, 82C can be defined in different ways depending on the specific configuration of the patient support apparatus 30. In the illustrated embodiment, the back egress configuration 80B may be defined as a "raised" configuration to support the patient in a fowlers position, and the leg egress configuration 82B may be likewise defined as a "raised" configuration to further support the patient in a modified fowlers position. Put differently, moving a side rail into a "raised" configuration does not necessarily require vertical movement of the side rail. As shown in FIG. 8, the leg ingress configuration 82C may also be defined as a further "raised" configuration (compare FIG. 8 to FIG. 7) employed to support the patient in another, further modified fowlers position. It will be appreciated that the back deck actuator 80 can be configured to move to any suitable back rest configuration, and the leg deck actuator 82 can be configured to move to any suitable leg rest configuration.

In the representative embodiment illustrated herein, the back deck actuator 80 and the leg deck actuator 82 are each realized as linear actuators disposed in force-translating relationship between their respective deck sections 40 and the intermediate frame 36. More specifically, the back deck actuator 80 is provided between the intermediate frame 36 and the back section 44, and the leg deck actuator 82 is provided between the intermediate frame 36 and the leg section 48. Each of the actuators 80, 82 is arranged for independent movement to position the respective deck sections 40 to adjust the shape of the patient support surface 42. Put differently, the articulation system 78 is configured to move the patient support deck 38, between a plurality of deck configurations including a flat deck configuration 78A (see FIG. 3), a fowlers deck configuration 78B (see FIGS. 4-5), an egress deck configuration 78C (see FIGS. 6-7), and an ingress deck configuration 78D (see FIG. 8). Other deck configurations are contemplated.

Those having ordinary skill in the art will appreciate that the patient support apparatus 30 could employ any suitable number of deck actuators 80, 82, of any suitable type or configuration sufficient to effect selective movement of the deck sections 40 relative to the support structure 32. By way of non-limiting example, the deck actuators 80, 82 could be linear actuators or one or more rotary actuators driven electronically and/or hydraulically, and/or controlled or driven in any suitable way. Moreover, the deck actuators 80, 82 could be mounted, secured, coupled, or otherwise operatively attached to the intermediate frame 36 and to the deck sections 40, either directly or indirectly, in any suitable way. In addition, one or more of the deck actuators 80, 82 could be omitted for certain applications. Furthermore, while the foot section 50 moves concurrently with the leg section 48 and is articulable relative thereto in response to movement of the leg deck actuator 82, it will be appreciated that the foot section 50 could be provided with a dedicated deck actuator in some embodiments.

With continued reference to FIGS. 1-8, the patient support apparatus 30 employs a control system, generally indicated at 84, to effect operation of various functions of the patient support apparatus 30, as described in greater detail below. To this end, and as is shown schematically in FIG. 2, the control system 84 generally comprises a controller 86 disposed in communication with one or more user interfaces 88 adapted for use by the patient and/or the caregiver to facilitate operation of one or more functions of the patient support apparatus 30 and/or other devices typically utilized in patient healthcare settings (for example, television controls). In certain embodiments, the controller 86 is also disposed in communication with the lift actuators 74, 76, the deck actuators 80, 82, and with various sensors employed to determine certain operating conditions of the patient support apparatus 30 and/or changes in patient status, behavior, position, condition, and the like as is described in greater detail below.

Figure 2:
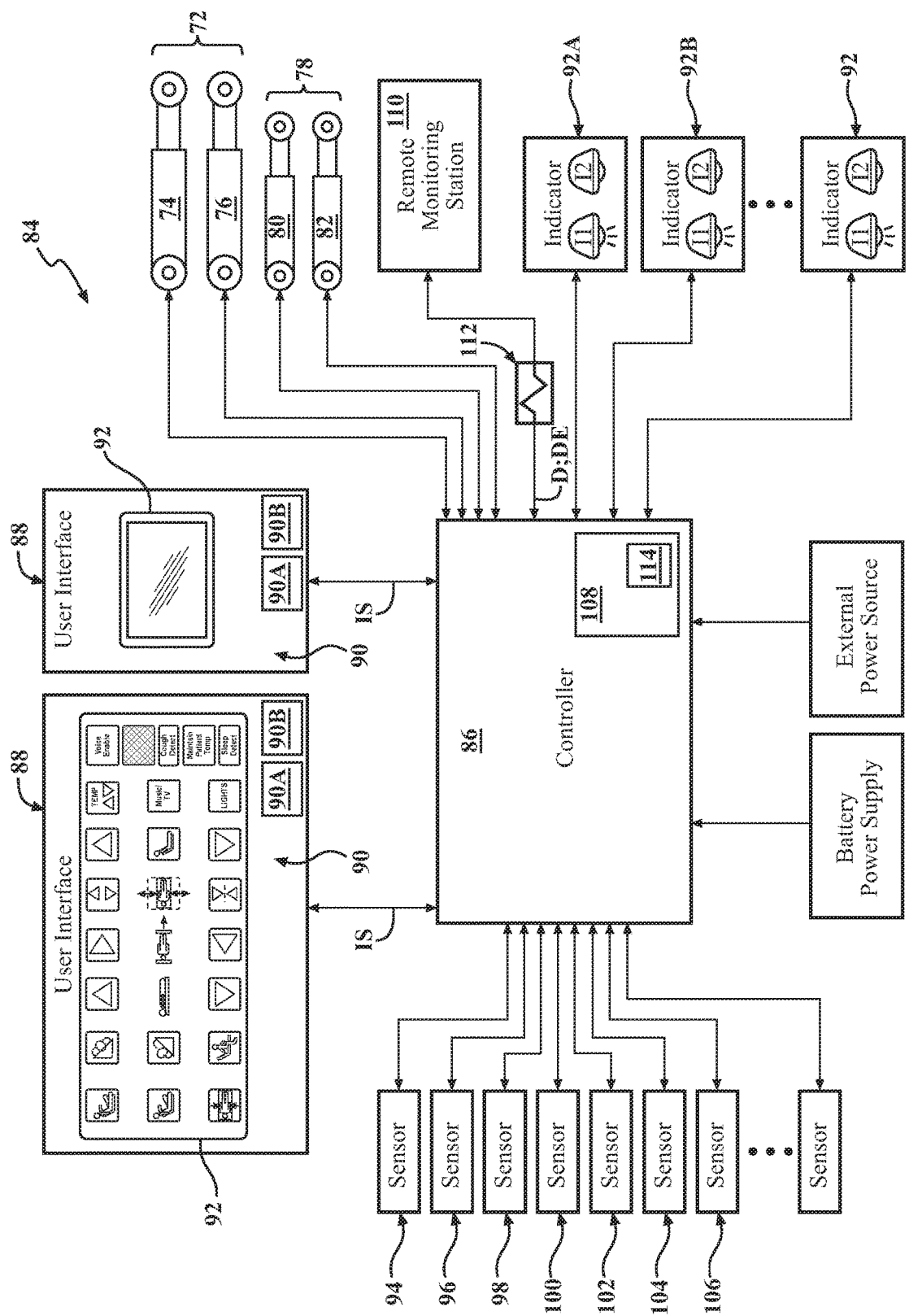
FIG. 2 is a schematic view of a control system of the patient support apparatus of FIG. 1.

As noted above, the controller 86 is best depicted schematically in FIG. 2, and has been omitted from certain drawings for clarity. It will be appreciated that the controller 86 and/or the control system 84 can be configured or otherwise arranged in a number of different ways, depending on the specific configuration of the patient support apparatus 30. The controller 86 may have one or more microprocessors for processing instructions or for processing an algorithm stored in memory to control operation of the actuators 74, 76, 80, 82, communication with the user interfaces 88, sensors, and the like. Additionally or alternatively, the controller 86 may comprise one or more microcontrollers, field programmable gate arrays, systems on a chip, discrete circuitry, and/or other suitable hardware, software, or firmware that is capable of carrying out the various functions and operations described herein. The controller 86 may be carried on-board the patient support apparatus 30, such as on the base 34, or may be remotely located. The controller 86 may comprise one or more subcontrollers configured to control the actuators 74, 76, 80, 82, sensors, and/or user interfaces 88 or one or more subcontrollers for each actuator 74, 76, 80, 82, sensor, and/or user interface 88. The controller 86 may communicate with the actuators 78, 80, sensors, user interfaces 88, or other systems or components via wired or wireless connections.

It will be appreciated that patient support apparatus 30 may comprise more than one user interface 88, positioned and/or configured so as to be accessible by the patient, by the caregiver, or by both the caregiver and the patient. The user interface 88 of the patient support apparatus 30 generally comprises an input device 90 configured to generate an input signal IS in response to activation by a user which, in turn, is communicated to the controller 86. The controller 86 is responsive to the input signal IS and can control or otherwise carry out one or more functions of the patient support apparatus 30 in response to receiving the input signal IS. Put differently, the controller 86 is configured to perform a function of the patient support apparatus 30 in response to receiving the input signal IS from the input device 90. By way of non-limiting example, the input device 90 could be realized as a "lift bed" button, activation of which causes the controller 86 to drive the lift actuators 74, 76 to move the patient support deck 38 and the intermediate frame 36 vertically away from the base 34. Those having ordinary skill in the art will appreciate that the input device 90 of the user interface 88 could be configured in a number of different ways sufficient to generate the input signal IS.

In certain embodiments, as described in greater detail below, the user interface 88 may also comprise indicators 92 configured to communicate information to the user, such as an operating condition of the patient support apparatus 30 itself, a status condition of the patient, and the like. It will be appreciated that indicators 92 could be utilized, configured, and/or arranged in a number of different ways sufficient to communicate information to the patient and/or the caregiver. Here too, it will be appreciated that the user interface 88 could similarly be provided in a number of different styles, shapes, configurations, and the like. By way of non-limiting example, the user interface 88 could be realized as a touchscreen which serves as both an input device 90 (for example, a capacitive touch interface) and an indicator 92 (for example, a display screen). Additionally, one or more user interfaces 88 could be implemented with a discrete indicator 92 but without a dedicated, localized input device 90 (for example, a light emitting diode (LED) coupled to a side rail), or vice-versa (for example, a button coupled to a side rail). Thus, it will be appreciated that the user interface 88 could comprise a number of indicators 92 and/or input devices 90 each coupled to the same or different components or structural features of the patient support apparatus 30 in certain embodiments.

With continued reference to FIG. 2, as noted above, the patient support apparatus 30 utilizes various sensors disposed in communication with the controller 86 to monitor operating conditions of the patient support apparatus 30 and/or status conditions of the patient. In some embodiments, the patient support apparatus 30 comprises a patient sensor 94 to determine the presence and/or position of the patient supported on the patient support deck 38. To this end, the patient sensor 94 may comprise one or more load cells disposed between the intermediate frame 36 and the patient support deck 38 which monitor changes in the patient's weight distribution about the patient support surface 42. However, it will be appreciated that the patient sensor 94 could be of any suitable type or configuration sufficient to determine the presence of and/or position of the patient, and could be disposed in any suitable location. By way of non-limiting example, the patient sensor 94 could be realized as a camera or sensor configured to determine a position and/or orientation of the patient on the patient support surface 42. Other types of patient sensors 94, such as those configured to respond to changes in the patient's status and/or vital signs, are contemplated.

In some embodiments, the patient support apparatus 30 comprises a head-end lift sensor 96 to determine movement of the head-end HE of the intermediate frame 36 between the head end positions 74A, 74B, 74C and a foot-end lift sensor 98 to determine movement of the foot-end FE of the intermediate frame 36 between the foot end positions 76A, 76B, 76C. Similarly, the patient support apparatus 30 may comprise a back deck sensor 100 to determine movement of the back deck actuator 80 between the back configurations 80A, 80B, and a leg deck sensor 102 to determine movement of the leg deck actuator 82 between the leg configurations 82A, 82B, 82C. Further, the patient support apparatus 30 may comprise a head-end side rail sensor 104 to determine movement of one of the first and third side rails 54, 58 between the side rail positions SR, SL, SI, and a foot-end side rail sensor 106 to determine movement of one of the second and fourth side rails 56, 60 between the side rail positions SR, SL, SI. Those having ordinary skill in the art will appreciate that the lift sensors 96, 98, the deck sensors 100, 102, and/or the side rail sensors 104, 106 are disposed in communication with the controller 86 and could be realized in a number of different ways, such as with one or more linear potentiometers, range sensors, hall-effect sensors, limit switches, accelerometers, gyroscopes, and the like generally configured or arranged to measure position, height, and/or movement. Further, certain sensors described above could be encoders, current sensors, and the like coupled to or in communication with one of the lift actuators 74, 76 and/or the deck actuators 80, 82. Moreover, it will be appreciated that the functionality afforded by the sensors described above could be entirely or partially realized with software or code for certain applications.

In one embodiment, the patient support apparatus 30 comprises a bed detection system, generally indicated at 108 in FIG. 2, which is configured to monitor data D associated with one or more of an operating condition of the patient support apparatus 30 and a status of the patient supported on the patient support deck 38, and to communicate these data D with a remote monitoring station, generally indicated at 110. As will be appreciated from the subsequent description below, the bed detection system 108 may comprise a discrete module, component, sub system, and the like which communicates with the controller 86 and/or various sensors described above. In the representative embodiment illustrated herein, the bed detection system 108 is formed as a part of the controller 86, which communicates data D with the remote monitoring station 110 across a network 112, such as a wired or wireless Ethernet network. Other configurations, communication protocols, and the like, are contemplated.

In some embodiments, the bed detection system 108 comprises a bed exit alarm system 114, whereby the data D communicated between the bed detection system 108 and the remote monitoring station 110 comprise bed exit alarm data DE. Here, via communication between the controller 86 and the patient sensor 94, the bed detection system 108 monitors the patient's position about the patient support surface 42 and is responsive to patient movement which indicates that the patient has exited the patient support apparatus 30 or is about to exit the patient support apparatus 30. By way of non-limiting example, where the patient sensor 94 comprises load cells to monitor the patient's weight distribution, a shift in weight to one side and/or end of the bed may indicate a pre-exit condition, and a change in the total weight may indicate an exit condition. The bed exit alarm system 114 is typically "disarmed" via an egress input 90A of the user interface 88, and "armed" via a resume input 90B of the user interface 88, which may be a discrete "button" separate from the egress input 90A in some embodiments, or may be realized as a "state" of the same "button" as the egress input 90A. Other configurations of the user interface 88 are contemplated.

One or more user interfaces 88 may be local to the patient support apparatus 30 and/or may be implemented into other devices remote from the patient support apparatus 30. Here, once the patient has completed ingress to the patient support apparatus 30, the caregiver actuates the resume input 90B to begin or resume monitoring for patient movement indicative of pre-exit or exit conditions and, if the patient attempts to exit the patient support apparatus 30 while the bed exit alarm system 114 of the bed detection system 108 is armed, the controller 86 communicates bed exit data DE to the remote monitoring station 110 to alert the caregiver. For example, the remote monitoring station 110 could respond to the bed exit data DE by sounding an alarm, sending a message to one or more caregivers, and the like. Similarly, the bed exit alarm system 114 could also be employed to activate other alarms, such as visual, audible, and/or tactile alarms coupled to the patient support apparatus 30, the remote monitoring station 110, a mobile device such as a tablet computer, and the like.

In addition to the bed exit alarm system 114 described above, the bed detection system 108 could also communicate other data D with the remote monitoring station 110, such as data D representing the health, status, and/or condition of the patient (for example, vital signs). Furthermore, the bed detection system 108 could communicate data D associated with the patient support apparatus 30 itself, such as to allow caregivers or other personnel at the remote monitoring station 110 to observe the location or movement of the patient support apparatus 30, the orientation of the articulation system 78, the orientation of the lift mechanism 72, and the like. Other configurations are contemplated. The Applicant has described additional details and features of one type of bed detection system in U.S. Pat. No. 8,689,376 B2, the disclosure of which is hereby incorporated by reference in its entirety. Other configurations are contemplated.

Referring again to FIGS. 1-8, in one embodiment, the egress input 90A of the user interface 88 cooperates with the controller 86 to facilitate placing the patient support apparatus 30 in a condition which promotes patient egress in a simple and efficient manner. Here, when the caregiver actuates the egress input 90A, the controller 86 interrupts communication of the bed detection system 108 with the remote monitoring station 110, drives the articulation system to move one or more of the deck sections 40 of the patient support deck 38 into the egress deck configuration 78C (see FIGS. 6-7), and drives the lift mechanism 72 to move the patient support deck 38 to the egress lift configuration 72C (see FIG. 7). Thus, via "one-touch" actuation of the egress input 90A, the caregiver is able to prevent inadvertent activation of the bed exit alarm system 114, drive the lift mechanism 72 to position the patient support deck 38 relative to the floor surface F at a height that is advantageous for patient ambulation, and drive the articulation system 78 to arrange the deck sections 40 into a configuration that is advantageous for patient ambulation with "one-touch" of the egress input 90A. Put differently, the caregiver does not have to sequentially actuate multiple, discrete input devices 90 to disarm the bed exit alarm system 114, adjust the lift mechanism 72, and adjust the articulation system 78 when assisting the patient with egress and ambulation to the floor surface F.

As noted above, activation of the egress input 90A by the user interrupts communication between the bed detection system 108 and the remote monitoring station 110. Put differently, activation of the egress input 90A advantageously "disarms" the bed exit alarm system 114 during, preceding, or immediately following movement of the lift mechanism 72 to the egress lift configuration 72C and/or movement of the articulation system 78 to the egress deck configuration 78C. Here, because the caregiver does not need to actuate multiple discrete input devices 90 to position the patient for ambulation, scenarios where the bed exit alarm system 114 is mistakenly left on while the caregiver is helping the patient with egress are avoided. It will be appreciated that inadvertent activation of the bed exit alarm system 114 is disadvantageous and has the potential to startle the patient mid-way through egress. Thus, the "one-touch" functionality afforded by the egress input 90A promotes enhanced patient care while, at the same time, enhancing caregiver usability of the patient support apparatus 30. As will be appreciated from the subsequent description below, the term "interrupts" is used herein to describe a change in the operation of the bed exit alarm system 114 and does not necessarily mean that all or even some communication is "stopped" between the bed detection system 108 and the remote monitoring station 110. On the contrary, activation of the egress input 90A may result in a different type of electronic communication between the bed detection system 108 and the remote monitoring station 110, such as an "interrupt" signal being communicated between and/or interpreted by the remote monitoring station 110 and/or the bed detection system 108 to prevent activation of the bed exit alarm system 114 during patient egress following activation of the egress input 90A.

Once the patient has egressed from the patient support apparatus 30, it is advantageous to subsequently "arm" the bed exit alarm system 114 or otherwise restore communication between the bed detection system 108 and the remote monitoring station 110, in particular after the patient returns to the patient support apparatus 30 and completes ingress, as is described in greater detail below. To this end, in one embodiment, the controller 86 is configured to restore communication between the bed detection system 108 and the remote monitoring station 110 when the patient sensor 94 subsequently determines the patient is supported by the patient support deck 38. In some embodiments, rather than arming the bed exit alarm system 114 and/or restoring communications between the bed detection system 108 and the remote monitoring station 110, the controller may be configured to prompt the caregiver, such as via an indicator 92, to manually arm the bed exit alarm system 114. Thus, the controller may be further configured to restore communication between the bed detection system 108 and the remote monitoring station 110 in response to actuation of the resume input 90B. Furthermore, in some embodiments, the controller 86 is configured to automatically arm and/or restore communications between the bed detection system 108 and the remote monitoring station 110 after a predetermined period following patient egress has lapsed. By way of illustration, the caregiver may activate the egress input 90A and help the patient to a bathroom before leaving the patient alone in the bathroom. If the patient falls, becomes unresponsive, or is otherwise away from the patient support apparatus 30 for an extended period of time exceeding the predetermined period, arming the bed exit alarm system 114 and/or restoring communications between the bed detection system 108 and the remote monitoring station 110 may advantageously alert the caregiver or other users that the patient has been away from the patient support apparatus 30 for too long and potentially requires assistance. Other configurations and scenarios are contemplated.

Figure 7:
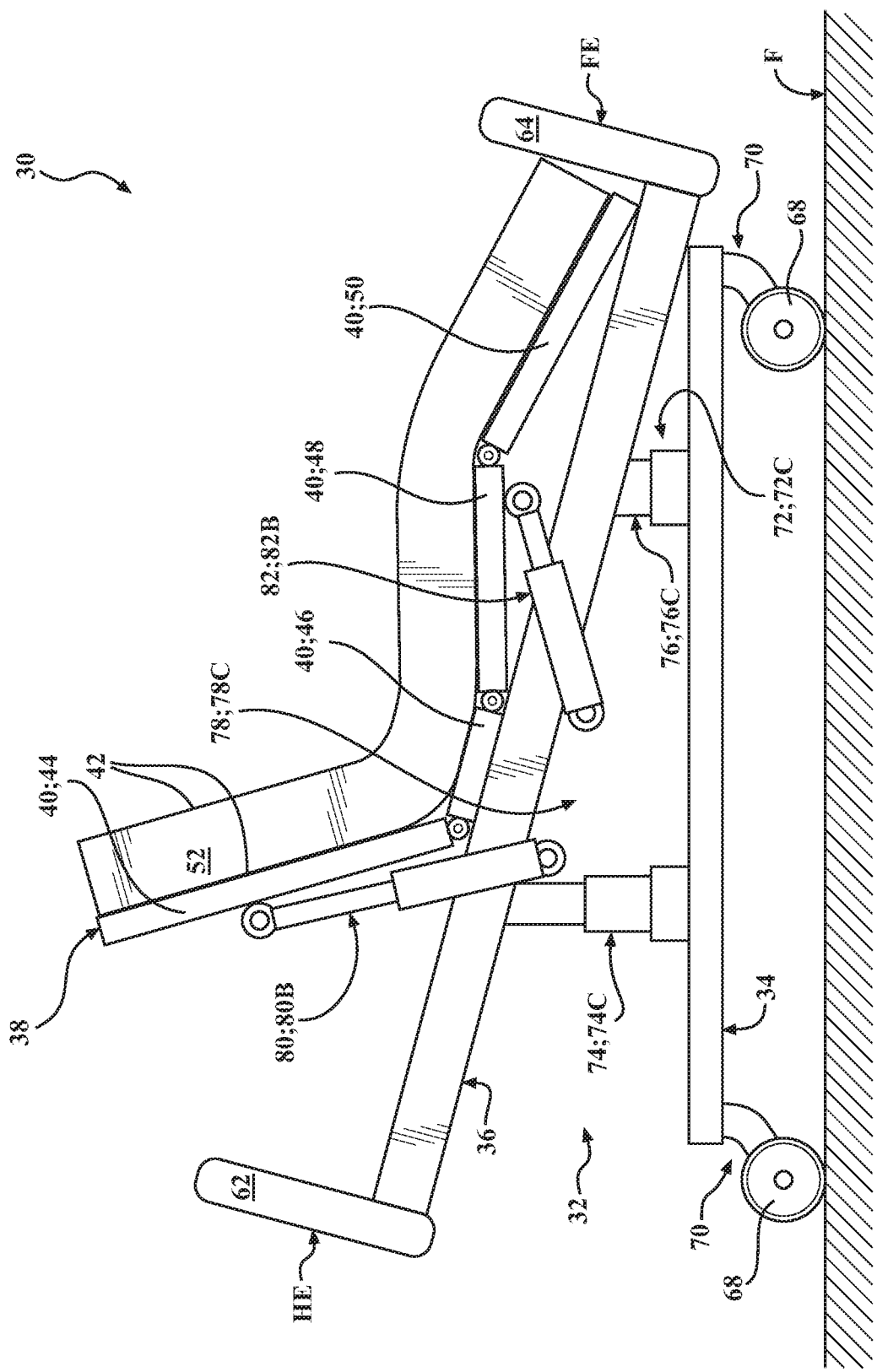
FIG. 7 is another right-side view of the patient support apparatus of FIGS. 3-6, shown with the lift mechanism supporting the patient support deck in a reverse Trendelenburg configuration, and shown with the patient support deck arranged to support the patient in the modified fowlers position.

As noted above, in the representative embodiment illustrated in FIG. 7, the egress lift configuration 72C of the lift mechanism 72 and the egress deck configuration 78C of the articulation system 78 are advantageously implemented in connection with patient support apparatuses 30 which are configured such that positioning the lift actuators 74, 76 at their respective lowered positions 74B, 76B (depicted in FIGS. 5-6) may be too low for the patient to egress from and ingress to the patient support apparatus 30 easily. Here, when the egress input 90A is actuated by the caregiver, movement of the lift mechanism 72 to the egress lift configuration 72C is further defined by the controller 86 driving the head-end lift actuator 74 to move the head end HE of the intermediate frame 36 to the egress head-end position 74C, and driving the foot-end lift actuator 76 to move the foot end FE of the intermediate frame 36 to the egress foot-end position 76C. This configuration places the intermediate frame 36 into a slight reverse Trendelenburg configuration irrespective of the orientation of the articulation system 78 (compare FIG. 7 to FIG. 6). Here too in the embodiment illustrated in FIG. 7, the controller 86 also adjusts the articulation system 78 so as to advantageously position the patient for egress from the patient support apparatus 30 by moving to the egress deck configuration 78C. More specifically, in the representative embodiment illustrated herein, movement of the articulation system 78 to the egress deck configuration 78C is further defined by the controller 85 driving the back deck actuator 80 to move the back section 44 to the back egress configuration 80B, and driving the leg deck actuator 82 to move the leg section 48 to the leg egress configuration 82B (see FIGS. 6-7; compare with FIGS. 5 and 3).

The egress lift configuration 72C and the egress deck configuration 78C depicted in FIG. 7 help position the patient's feet closer to the floor surface F than depicted in FIG. 5 where the leg deck actuator 82 positions the leg section 48 and the foot section 50 in the leg flat configuration 82A and where the lift actuators 74, 76 are each in their respective lowered positions 74B, 76B. Thus, the patient support apparatus 30 is able to position the patient in ways which are advantageous for ambulation to the floor surface F by bringing their feet as close as possible to the floor surface F while providing a stable patient support surface 42 to sit upward from. More specifically, and with continued reference to FIG. 7, in the illustrated embodiment, the leg section 48 of the patient support deck 38 is substantially parallel with the floor surface F when the head end HE of the intermediate frame 36 is in the egress head-end position 74C, when the foot end FE of the intermediate frame 36 is in the egress foot-end position 76C, when the back section 44 is in the back egress configuration 80B, and when the leg section 48 is in the leg egress configuration 82B. Here too, the foot end FE of the intermediate frame 36 is closer to the floor surface F than the back section 40 of the patient support deck 38 when the head end HE of the intermediate frame 36 is in the egress head-end position 74C, when the foot end FE of the intermediate frame 36 is in the egress foot-end position 76C, when the back section 44 is in the back egress configuration 80B, and when the leg section 48 is in the leg egress configuration 82B.

Figure 3:
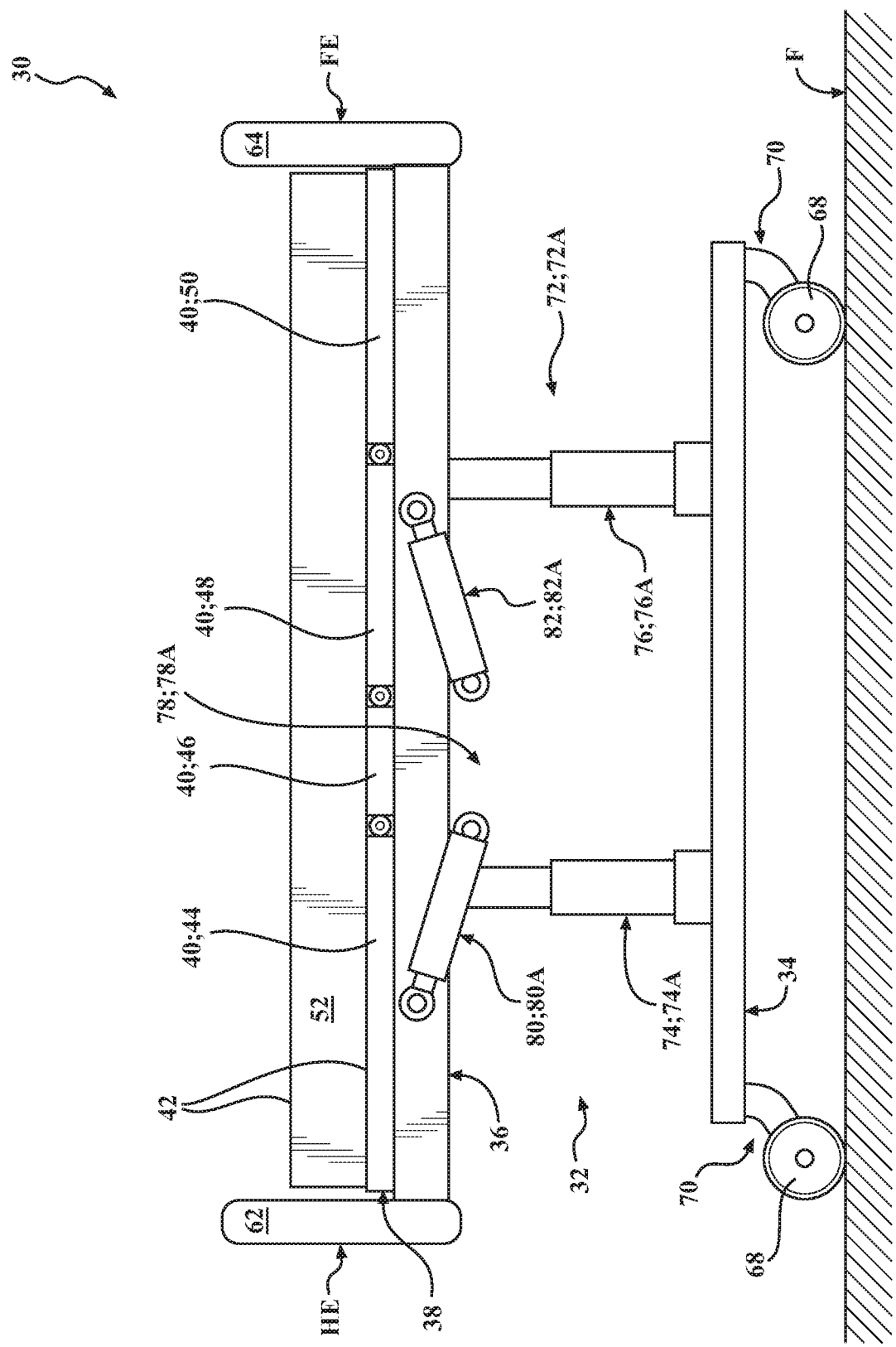
FIG. 3 is a right-side view of a patient support apparatus show having a base, a patient support deck, and a lift mechanism supporting the patient support deck in a first vertical configuration, shown with the patient support deck arranged to support a patient in a flat position.
Figure 4:
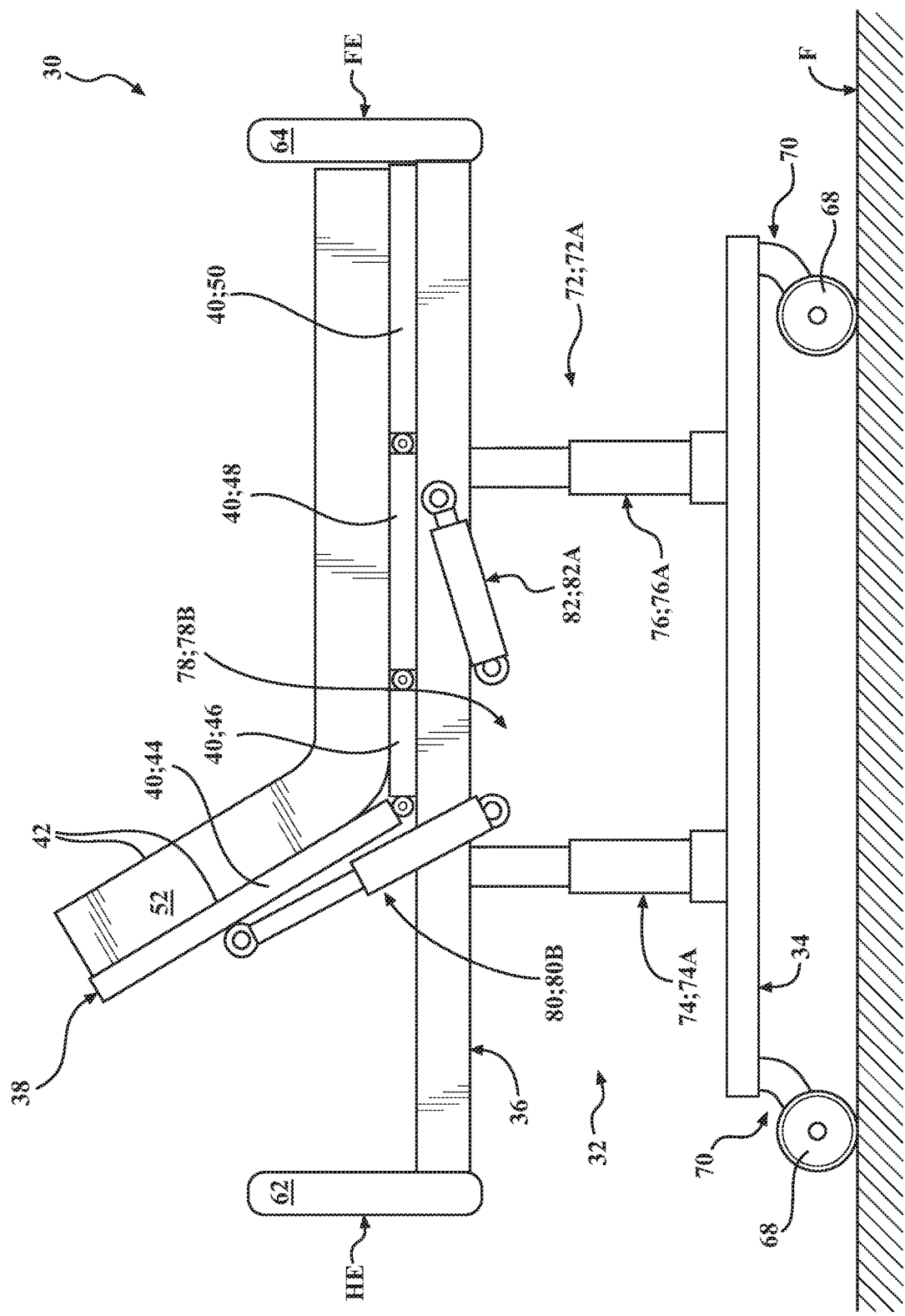
FIG. 4 is another right-side view of the patient support apparatus of FIG. 3, shown with the lift mechanism supporting the patient support deck in the first vertical configuration, and shown with the patient support deck arranged to support the patient in a fowlers position.

Referring again to FIGS. 1-8, it will be appreciated that the controller 86 can be configured in a number of different ways to facilitate moving the lift mechanism 72 to the egress lift configuration 72C and the articulation system 78 to the egress deck configuration 78C. In one embodiment, the controller 86 is configured to independently and sequentially drive the actuators 74, 76, 80, 82 in response to actuation of the egress input 90A. By way of illustrative example, if the patient support apparatus 30 is arranged as depicted in FIG. 3, with the lift mechanism 70 in the raised lift configuration 72A and with the articulation system 78 in the flat deck configuration 78A, it is conceivable that the controller 86 could first drive the back deck actuator 80 to move the back section 44 from the back flat configuration 80A (see FIG. 3) to the back egress configuration 80B (see FIG. 4) before driving the leg deck actuator 82 or either of the lift actuators 74, 76. Depending on the specific configuration of the patient support apparatus 30, it may be advantageous to drive certain actuators 74, 76, 80, 82 before others. By way of illustrative example, in one embodiment, the controller 86 is configured to drive the leg deck actuator 82 to move the leg section 48 of the patient support deck 38 to the leg egress configuration 82B prior to driving the foot-end lift actuator 76 and/or the head-end lift actuator 74. However, those having ordinary skill in the art will appreciate that the controller 86 could be configured to drive the actuators 74, 76, 80, 82 in a number of different sequences, orders, and the like.

In one embodiment, the controller 86 is configured to simultaneously drive each of the lift actuators 74, 76 and each of the deck actuators 80, 82 toward their respective egress positions 74C, 76C and egress configurations 80C, 82C. In some embodiments, the controller 86 is configured to drive each of the actuators 74, 76, 80, 82 at independent drive speeds to effect coordinated motion to the egress head-end position 74C, the egress foot-end position 76C, the back egress configuration 80B, and the leg egress configuration 82B. Here, by monitoring the positions of each of the actuators 74, 76, 80, 82 via the sensors 96, 98, 100, 102, the controller 86 is able to drive each actuator 74, 76, 80, 82 to arrive at the egress positions and configurations 74C, 76C, 80B, 82B together from wherever the actuators 74, 76, 80, 82 are positioned when the user actuates the egress input 90A. In some embodiments, the controller 86 is configured to drive each of the actuators 74, 76, 80, 82 at independent drive speeds such that movement into at least two of the egress head-end position 74C, the egress foot-end position 76C, the back egress configuration 80B, and the leg egress configuration 80C occurs substantially simultaneously. However, it will be appreciated that other configurations and types of coordinated movement are contemplated. By way of illustration, the controller 86 could coordinate movement of each of the lift actuators 74, 76, but drive the deck actuators 80, 82 sequentially.

In one embodiment, the controller 86 is configured to drive the articulation system 78 from the egress deck configuration 78C (see FIG. 7) to the ingress deck configuration 78D (see FIG. 8) after a predetermined period where the patient sensor 94 detects an absence of the patient on the patient support deck 38. In the representative embodiment illustrated herein, the ingress deck configuration 78D is similar to the egress deck configuration 78C, except for the orientation of the leg section 48 and the seat section 50 of the patient support deck 38. In order to move the articulation system 78 to the ingress deck configuration 78D, the controller 86 drives the leg deck actuator 82 so as to move the leg section 48 from the leg egress position 82B (see FIG. 7) to the leg ingress configuration 82C (see FIG. 8). In the leg ingress configuration 82C, the leg section 48 of the patient support deck 38 is no longer substantially parallel to the floor surface F (compare FIG. 8 to FIG. 7). Rather, as depicted in FIG. 8, the leg section 48 is elevated when the articulation system 78 is in the ingress deck configuration 78D. This arrangement helps guide the patient back to the proper position on the patient support surface 42 during ingress. More specifically, because the back section 44 and the leg section 48 are each raised or "tilted" relative to the seat section 46, the patient's body is guided toward the seat section 46 when sitting during ingress. Thus, sitting on the "tilted" back section 44 or leg section 48 is substantially avoided when the articulation system 78 is in the ingress deck configuration 78D depicted in FIG. 8.

Figure 8:
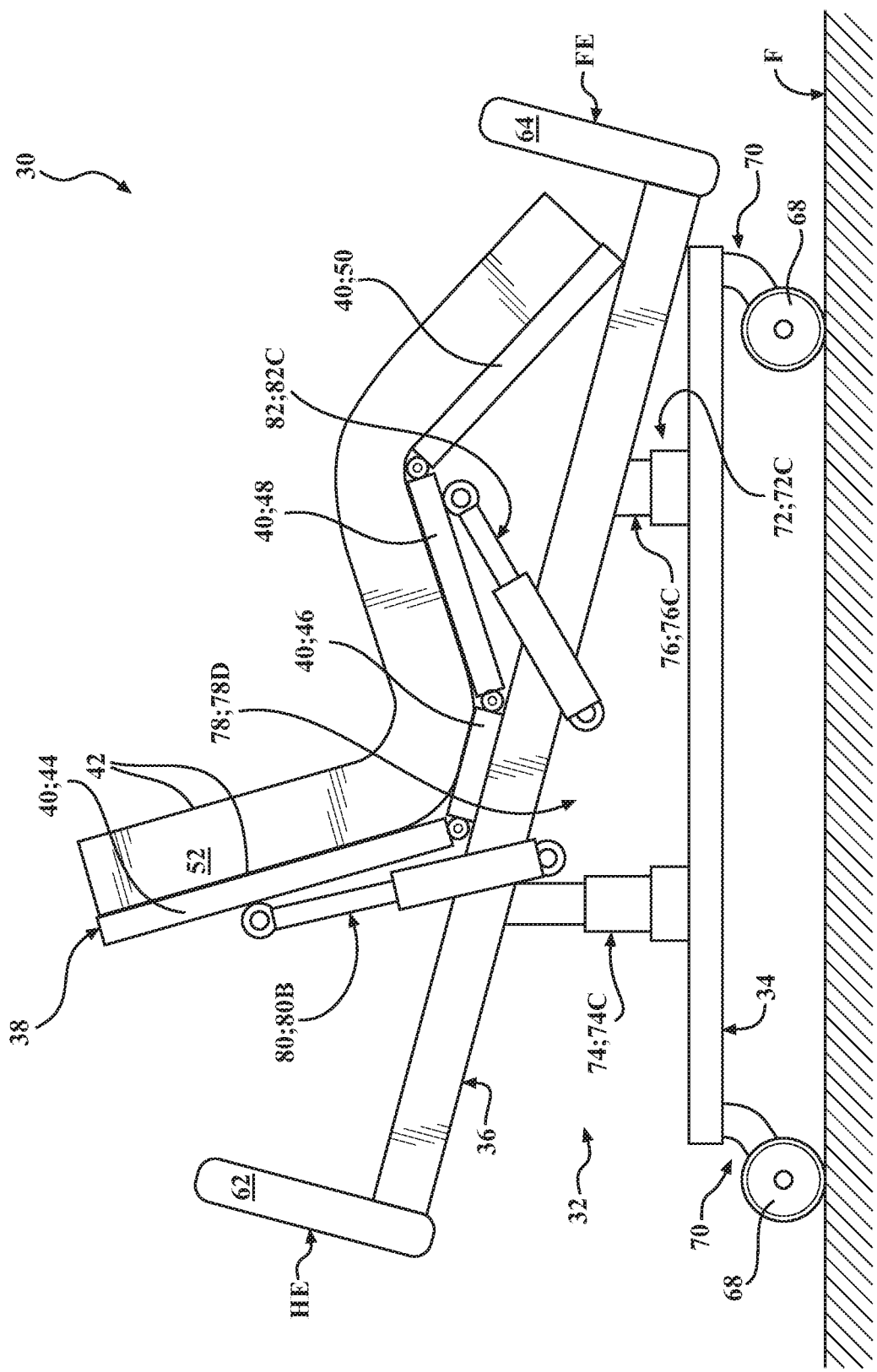
FIG. 8 is another right-side view of the patient support apparatus of FIGS. 3-6, shown with the lift mechanism supporting the patient support deck in a reverse Trendelenburg configuration, and shown with the patient support deck arranged to support the patient in another modified fowlers position.

In some embodiments, once the patient has initiated ingress from the floor surface F and has sat upon the portion of the patient support surface 42 between the "tilted" back section 44 and leg section 48 as depicted in FIG. 8, the controller 86 is further configured to return to the deck configuration depicted in FIG. 7 so as to ease the process of swinging the patient's legs onto the mattress 52 from the floor surface F. Here, it will be appreciated that the controller 86 could determine that the patient is sitting on the correct portion of the patient support surface 42 by using the patient sensor 94, as noted above.

Referring now to FIGS. 1-18, as noted above the patient support apparatus 30 comprises side rails 54, 56, 58, 60 to help control patient ingress and egress, whereby one or more of the side rails 54, 56, 58, 60 are generally movable between different side rail positions SR, SL, SI. In one embodiment, the patient support apparatus 30 is further configured to help guide the caregiver through the process of assisting the patient with egress to the floor surface F. To this end, and as is described below in connection with FIGS. 9-18, the controller activates different indicators 92 in response to the relative position of the side rails 54, 56, 58, 60 via the side rail sensors 104, 106, as well as the different configurations of the lift mechanism 72 and the articulation system 78 noted above.

As is depicted schematically in FIG. 2 and is described in connection with FIGS. 9-18 below, in one embodiment the patient support apparatus 30 comprises a foot-end side rail indicator 92A and a head-end side rail indicator 92B. In some embodiments, the foot-end side rail indicator 92A is coupled to the second side rail 56 and/or the fourth side rail 60, and the head-end side rail indicator 92B is coupled to the first side rail 54 and/or the third side rail 58, such that the side rail indicators 92A, 98B move concurrently with their respective side rail 56, 60, 54, 58 between the raised side rail position SR, the lowered side rail position SL, and the intermediate side rail position SI described above. However, it will be appreciated that each of the side rail indicators 92A, 92B could be located in common area, such as a display screen of a user interface 88. Furthermore, as will be appreciated from the subsequent description below, the side rail indicators 92A, 92B could be of a number of different types or arrangements suitable to communicate the position of the respective side rail 56, 60, 54, 58. By way of non-limiting example, the side rail indicators 92A, 92B could be discrete light-emitting diodes (LEDs) which are operable between different indication states, such as an "on" first indication state I1 and an "off" second indication state I2. Other configurations are contemplated, such as where the indication states I1, I2 are designated by different colors, sounds, haptic patterns, and the like. By way of non-limiting example, it is conceivable that the side rail indicators 92A, 92B could be implemented as discrete LEDs arranged to illuminate all or a portion of the respective side rails 56, 60, 54, 58, such as the grips 66. By way of further example, the side rail indicators 92A, 92B could be implemented as haptic modules to generate localized vibration at the grips 66 or other portions of the side rails 56, 60, 54, 58. Furthermore, as noted above, the side rail indicators 92A, 92B could be implemented as text-based prompts presented on a display screen of the user interface 88 which, as noted above, could be coupled to any suitable portion of the patient support apparatus 30, such as to the headboard 62, the footboard 64, and the like. Other arrangements and configurations are contemplated.

FIGS. 9-18 sequentially illustrate one way in which patient egress is carried out with the assistance of the caregiver. As will be appreciated from the subsequent description below, the reverse sequence (FIG. 18 to FIG. 9) could also be used to illustrate one way in which patient ingress is carried out with the assistance of the caregiver. However, for the purposes of clarity and consistency, the following description of FIGS. 9-18 will be made in connection with patient egress.

Figure 9:
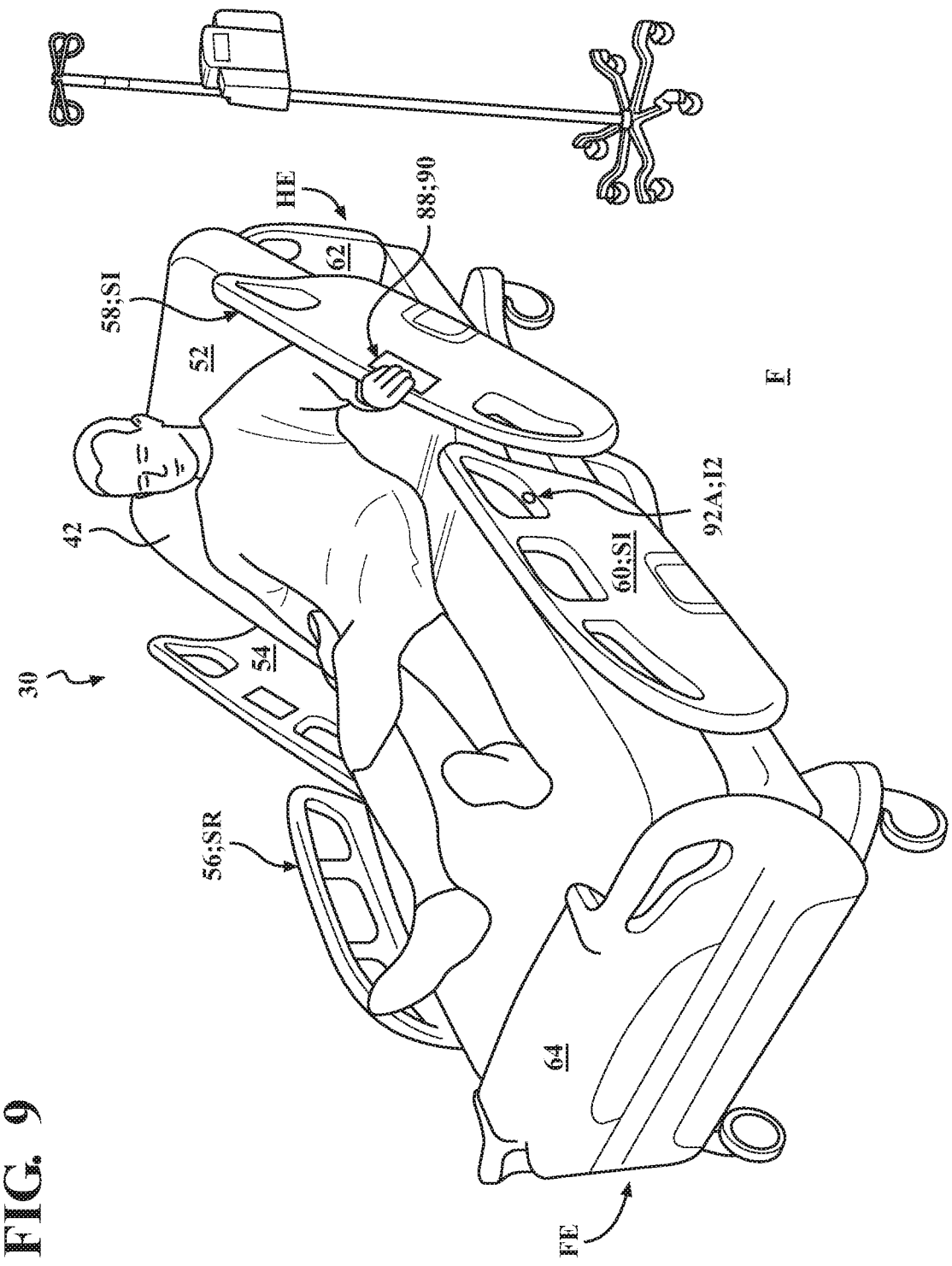
FIG. 9 is a perspective illustration of a patient supported in a patient support apparatus.
Figure 10:
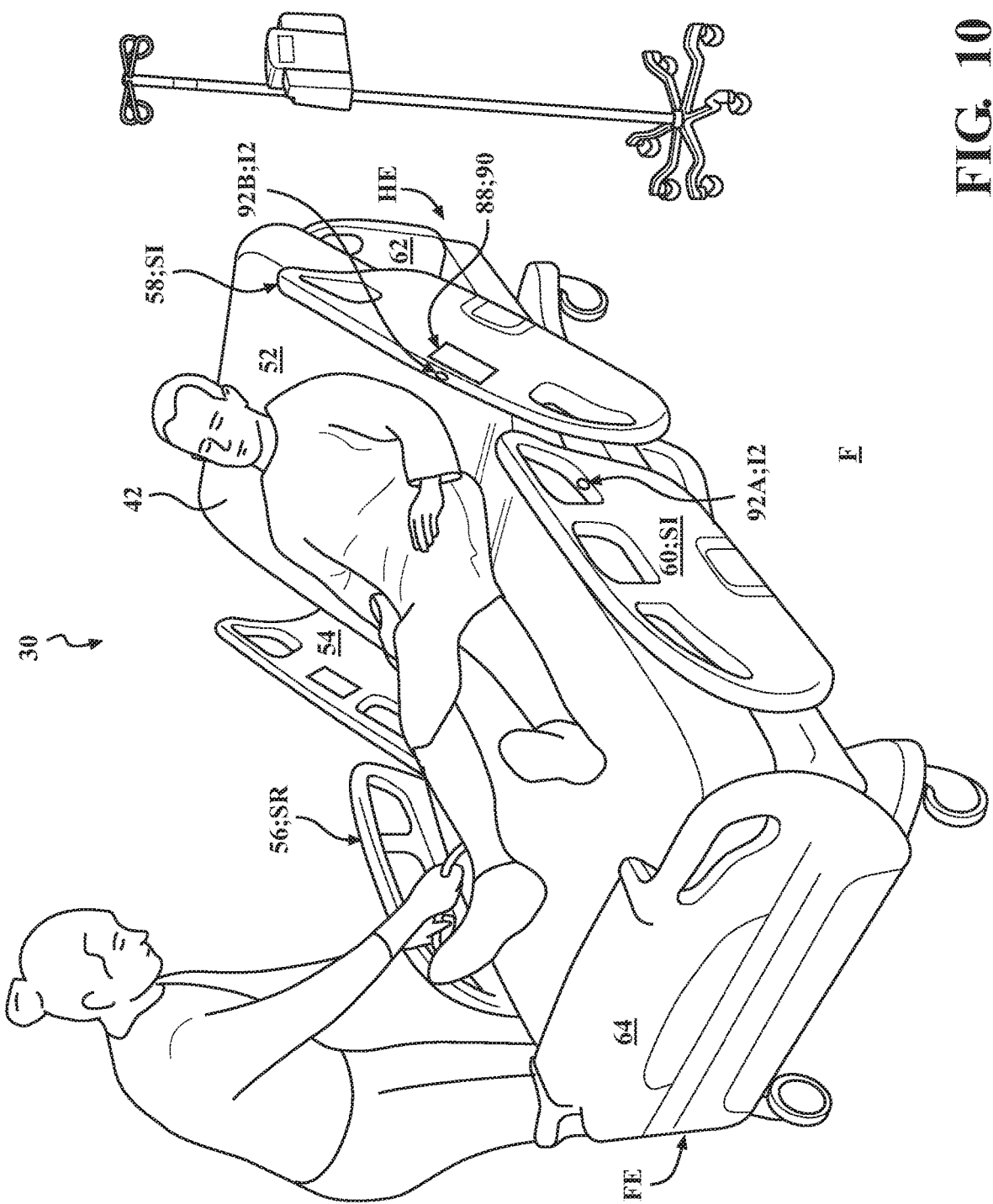
FIG. 10 is another perspective illustration of the patient and patient support apparatus of FIG. 9, depicting a caregiver preparing the patient for egress from the patient support apparatus.

In FIG. 9, the patient is shown laying in a fowlers position on the patient support apparatus 30. Here, the patient is also shown activating an input device 90 coupled to the third side rail 58 (arranged at the left head end HE) to get the caregiver's attention (for example, via a nurse call system). In FIG. 10, the caregiver is shown positioned adjacent to the patient support apparatus 30, and is preparing the patient for egress. In the illustrated example, the caregiver is disconnecting a deep vein thrombosis (DVT) system.

Figure 11:
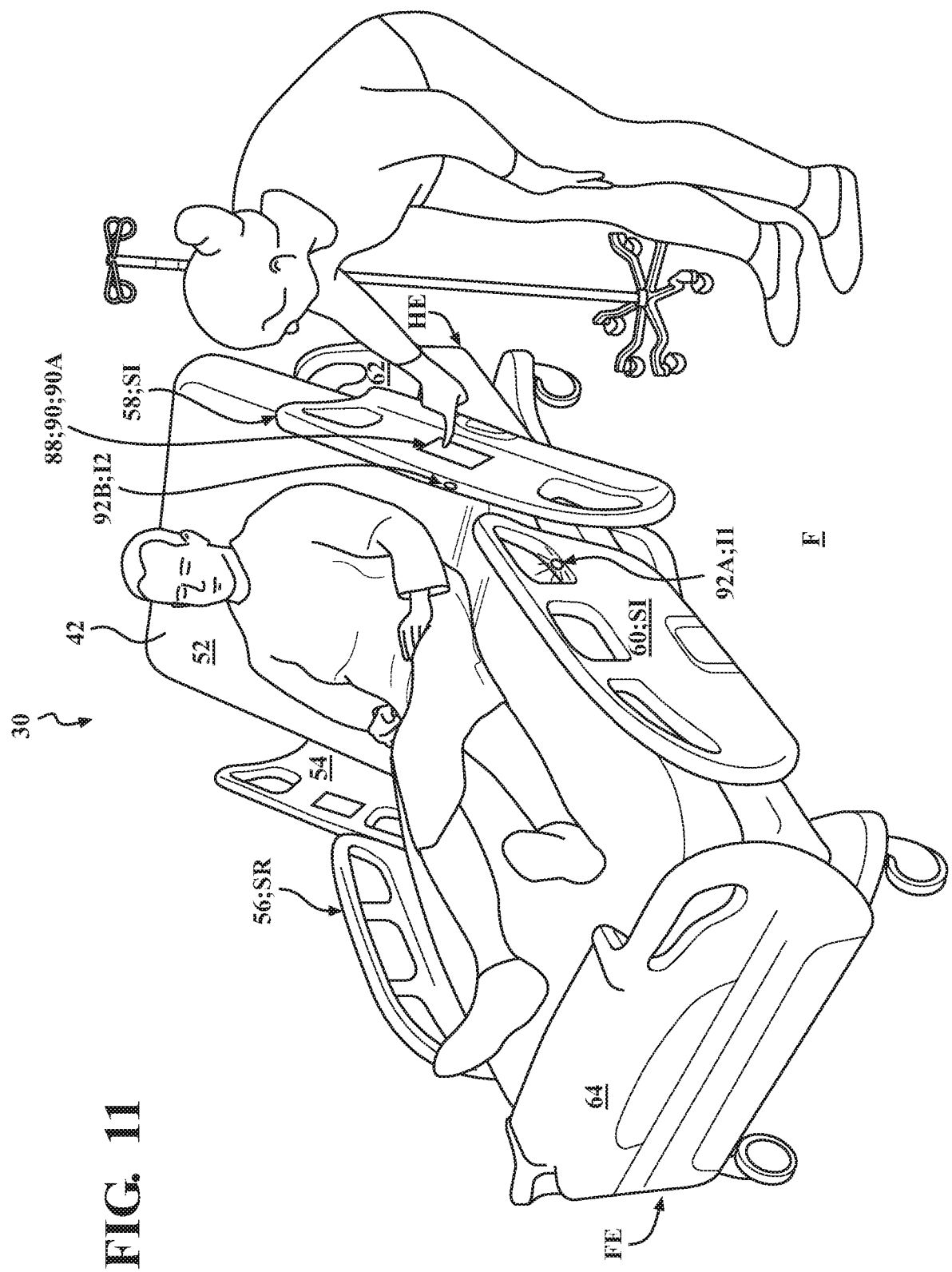
FIG. 11 is another perspective illustration of the patient and patient support apparatus of FIGS. 9-10, depicting the caregiver activating an egress input of the patient support apparatus.

In FIG. 11, the caregiver is shown actuating the egress input 90A to drive the lift mechanism 72 and/or the articulation system 78 to respective egress configurations 72C, 78C, with the patient support deck 38 positioned closer to the floor surface F and with the back section 44 tilted further toward the foot end FE (compare FIG. 11 to FIG. 10; positions and configurations not labeled). As noted above, the egress configurations 72C, 78C can be defined in different ways depending on the embodiment of the patient support apparatus 30. Thus, for the purposes of clarity and simplicity in connection with the illustrated embodiment depicted in FIGS. 9-18, the egress lift configuration 72C is defined as a suitable vertical configuration of the patient support deck 38 sufficient to promote ambulation, and the egress deck configuration 78C is defined as a suitable arrangement of deck sections 40 to promote ambulation.

With continued reference to FIG. 11, in this embodiment, the foot-end side rail indicator 92A is coupled to the fourth side rail 60 and is shown "on" in the first indication state I1.

In this exemplary embodiment, the foot-end side rail indicator 92A is implemented as a discrete LED which emits visible light in the first indication state I1 to prompt the caregiver to move the fourth side rail 60 as the next step in carrying out patient egress. Here, because the controller 86 knows the position of the fourth side rail 60 via the foot-end side rail sensor 106 (see FIG. 2), and because the controller 86 knows that patient egress is desired based on the activation of the egress input 90A, the controller 86 is configured to move the foot-end side rail indicator 92A from being "off" in the second indication state I2 (see FIG. 10) to being "on" in the first indication state I1 (see FIG. 11). Put differently, when the patient support deck 38 is moved to the egress lift configuration 72C via the lift mechanism 72 and to the egress deck configuration 78C via the articulation system 78 in response to activation of the egress input 90A, if the controller 86 determines that the fourth side rail 60 (at the foot-end and on the same side as the user interface) is in an undesired position concerning egress (for example, in a raised side rail position SR which blocks egress as depicted in FIG. 11), then the controller 86 activates the foot-end side rail indicator 92A to prompt the user to move the fourth side rail 60 to the lowered side rail position SL so as to facilitate patient egress. In some embodiments, such as those where the side rails 54, 56, 58, 60 are "motorized" or are otherwise provided with actuators (not shown) to facilitate automated movement of the side rails 54, 56, 58, 60, it will be appreciated that the controller 86 could be configured to drive one or more actuators to move the side rails 54, 56, 58, 60 automatically, as opposed to "prompting" the caregiver to move them manually. Here too, the controller 86 could request confirmation from the caregiver, such as via one or more indicators or via the user interface 88, to "confirm" that the respective side rail 54, 56, 58, 60 is ready to be moved with an actuator prior to actually moving the side rail 54, 56, 58, 60. Here, confirmation may be effected by actuation of an input device 90. Other configurations are contemplated. While the side rails 54, 56, 58, 60 may be manually moved by the caregiver or automatically moved via actuators driven by the controller 86, as noted above, for the purposes of clarity and consistency, subsequent description of side rail 54, 56, 58, 60 will be made with respect to manual movement by the caregiver.

Figure 12:
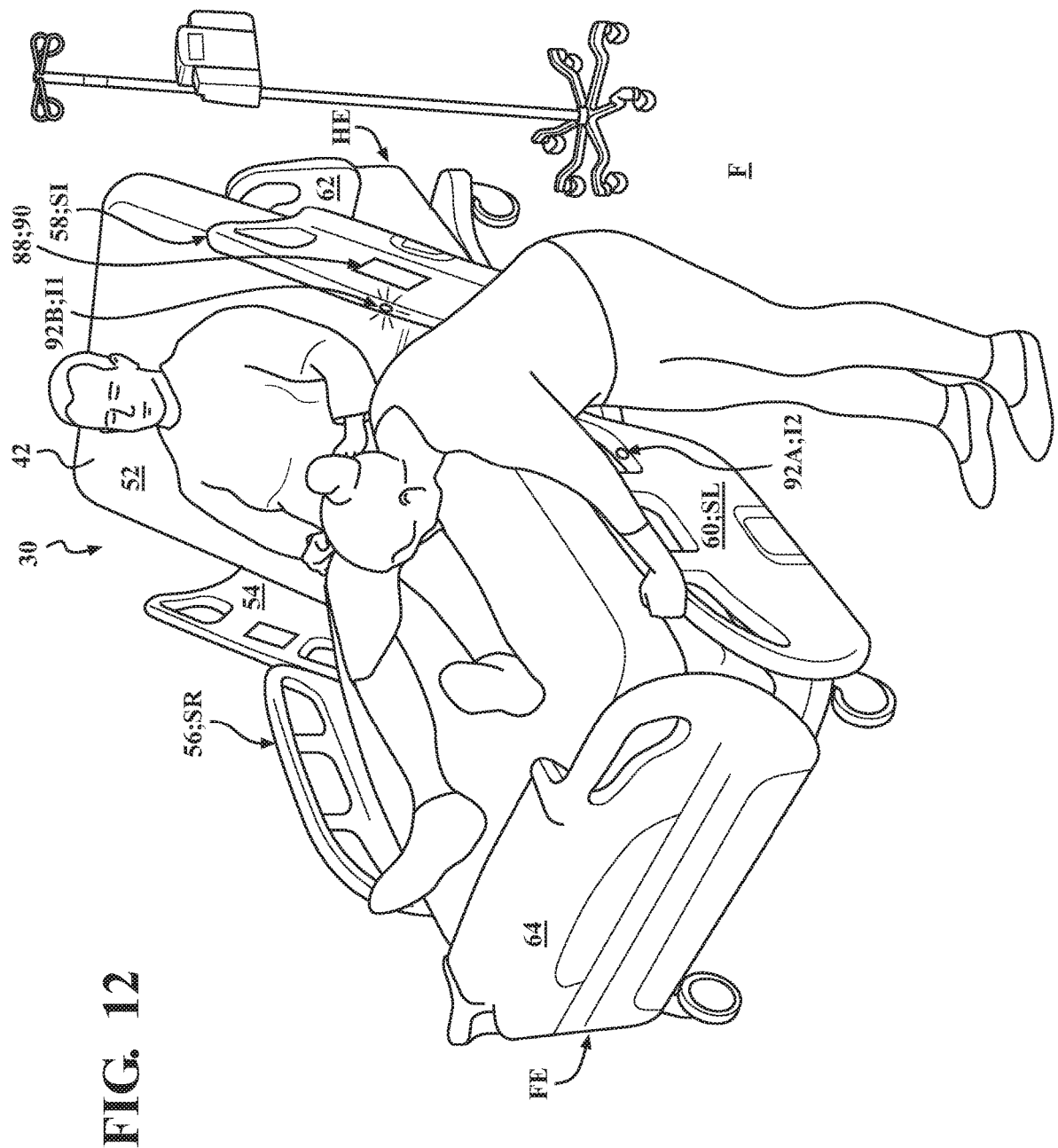
FIG. 12 is another perspective illustration of the patient and patient support apparatus of FIGS. 9-11, depicting the caregiver repositioning a foot-end side rail of the patient support apparatus.
Figure 13:
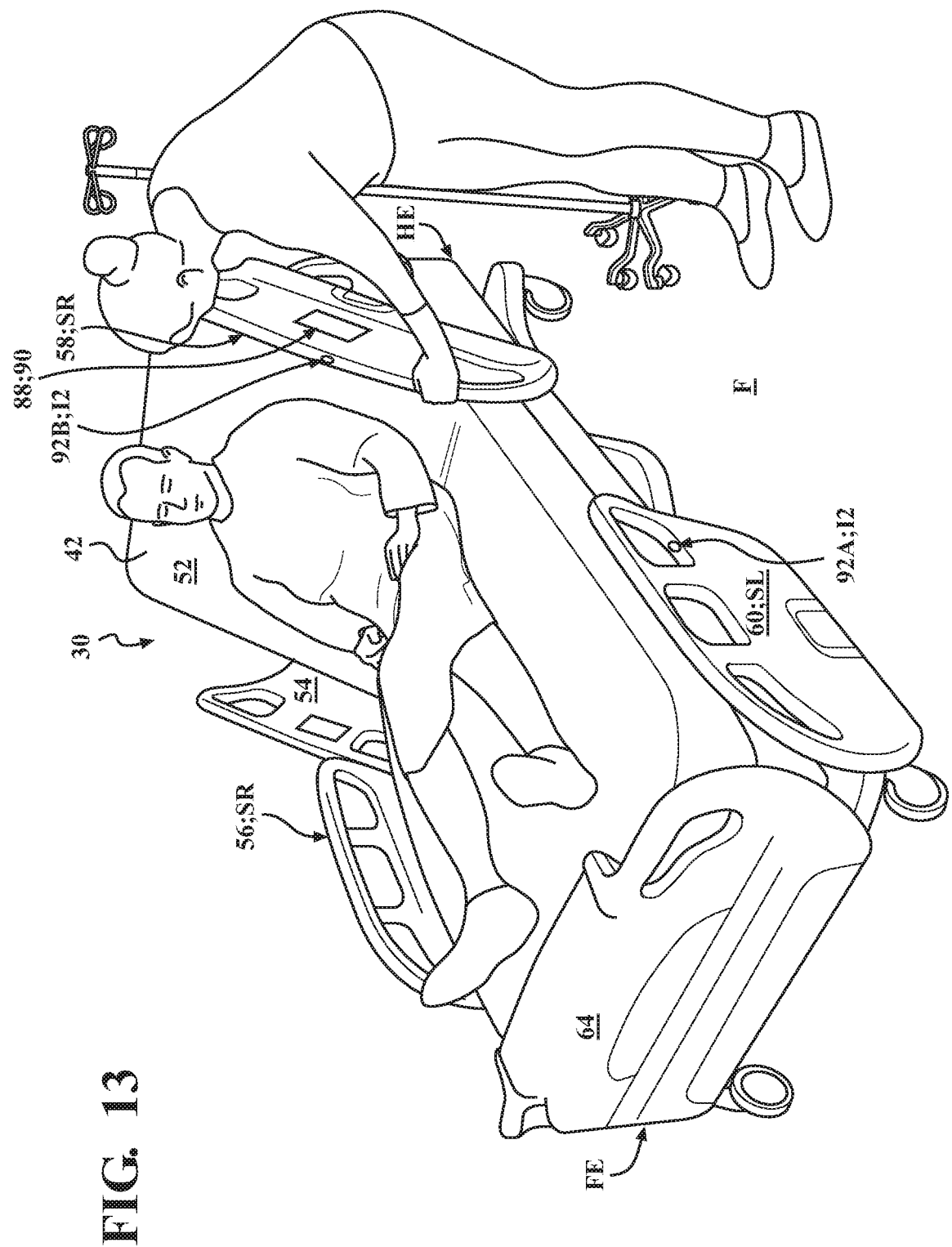
FIG. 13 is another perspective illustration of the patient and patient support apparatus of FIGS. 9-12, depicting the caregiver repositioning a head-end side rail of the patient support apparatus.

FIG. 12 depicts the caregiver having moved the fourth side rail 60 to its lowered side rail position SL. Here, the foot-end side rail indicator 92A has been deactivated via the controller 86 and is in the "off" second indication state I2 (compare FIG. 12 with FIG. 11). In addition, FIG. 12 also depicts the head-end side rail indicator 92B coupled to the third side rail 58, which here is shown "on" in the first indication state I1. In this part of the egress process, the head-end side rail indicator 92B is similarly implemented as a discrete LED which emits visible light in the first indication state I1 to prompt the caregiver to move the third side rail 58 as the next step in carrying out patient egress. Here, because the controller 86 knows the position of the third side rail 58 via the head-end side rail sensor 104 (see FIG. 2), and because the controller 86 knows that patient egress is desired based on the activation of the egress input 90A, the controller 86 is configured to move the head-end side rail indicator 92B from being "off" in the second indication state I2 (see FIG. 11) to being "on" in the first indication state I1 (see FIG. 12). Put differently, when the patient support deck 38 is moved to the egress lift configuration 72C via the lift mechanism 72 and to the egress deck configuration 78C via the articulation system 78 in response to activation of the egress input 90A, if the controller 86 determines that the third side rail 58 (at the head-end and on the same side as the user interface) is in an undesired position concerning egress (for example, in the lowered side rail position SL that limits patient access to the grip 66 as depicted in FIG. 12), then the controller 86 activates the head-end side rail indicator 92B to prompt the user to move the third side rail 58 to the raised side rail position SR or the intermediate side rail position SI so as to position the grip 66 of the third side rail 58 for use by the patient to facilitate patient egress. While the illustrative example described above and illustrated in FIGS. 12-13 depicts alerting the user to move the fourth side rail 60 prior to alerting the user to move the third side rail 58, it will be appreciated that the controller 86 could simultaneously put both side rail indicators 92A, 92B in the first indication state I1, whereby the user could move the side rails 58, 60 to the desired positions in any suitable order. Here, it will be appreciated that the controller 86 could be configured to activate one or more indicators 92, or otherwise prompt the caregiver, to move one or more of the side rails 54, 56, 58, 60 in a specific order or sequence, depending on the relative position of each of the side rails 54, 56, 58, 60 and whether patient ingress or patient egress is being carried out. Other configurations are contemplated.

Figure 14:
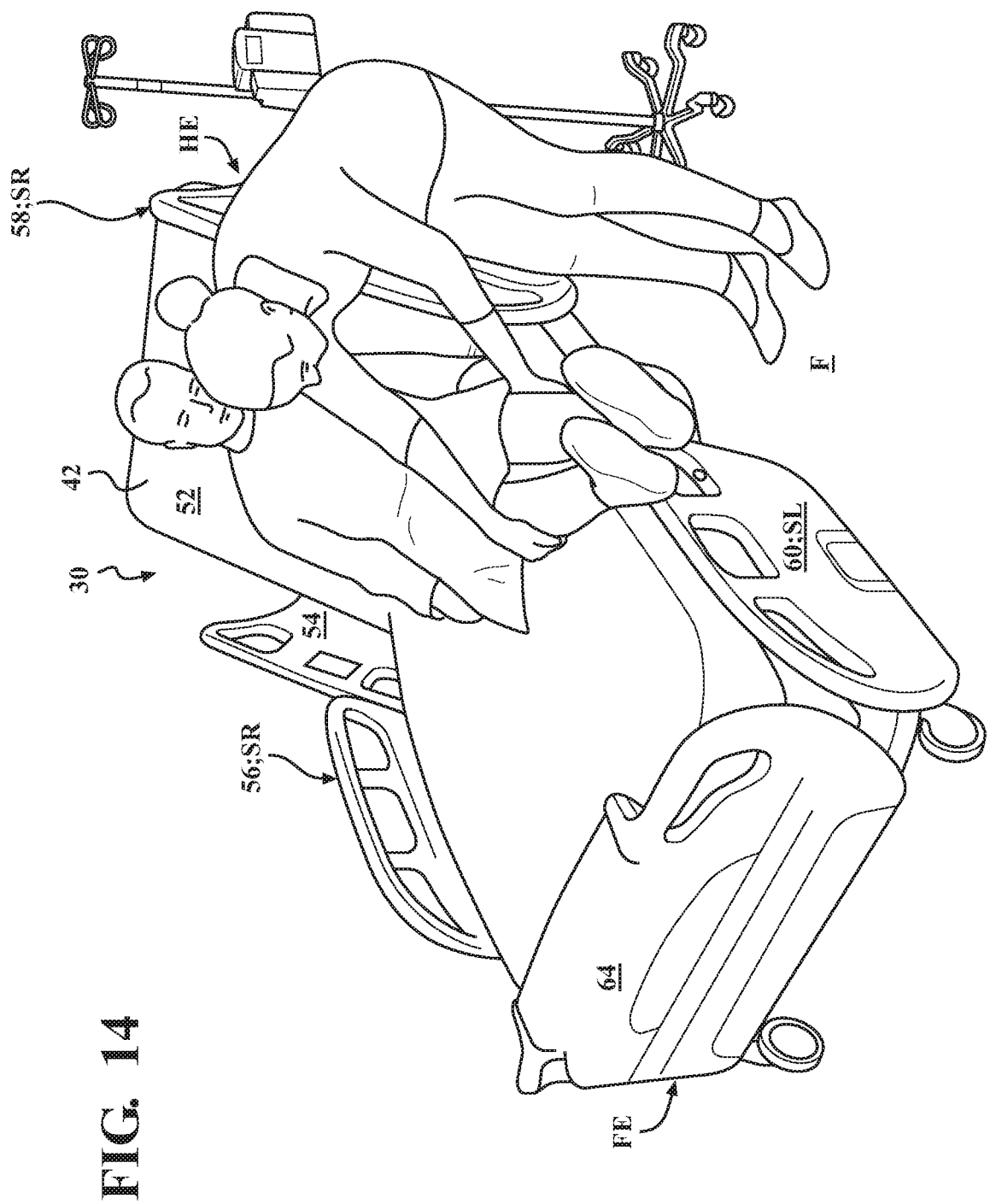
FIG. 14 is another perspective illustration of the patient and patient support apparatus of FIGS. 9-13, depicting the caregiver moving the patient's legs off the patient support apparatus.
Figure 15:
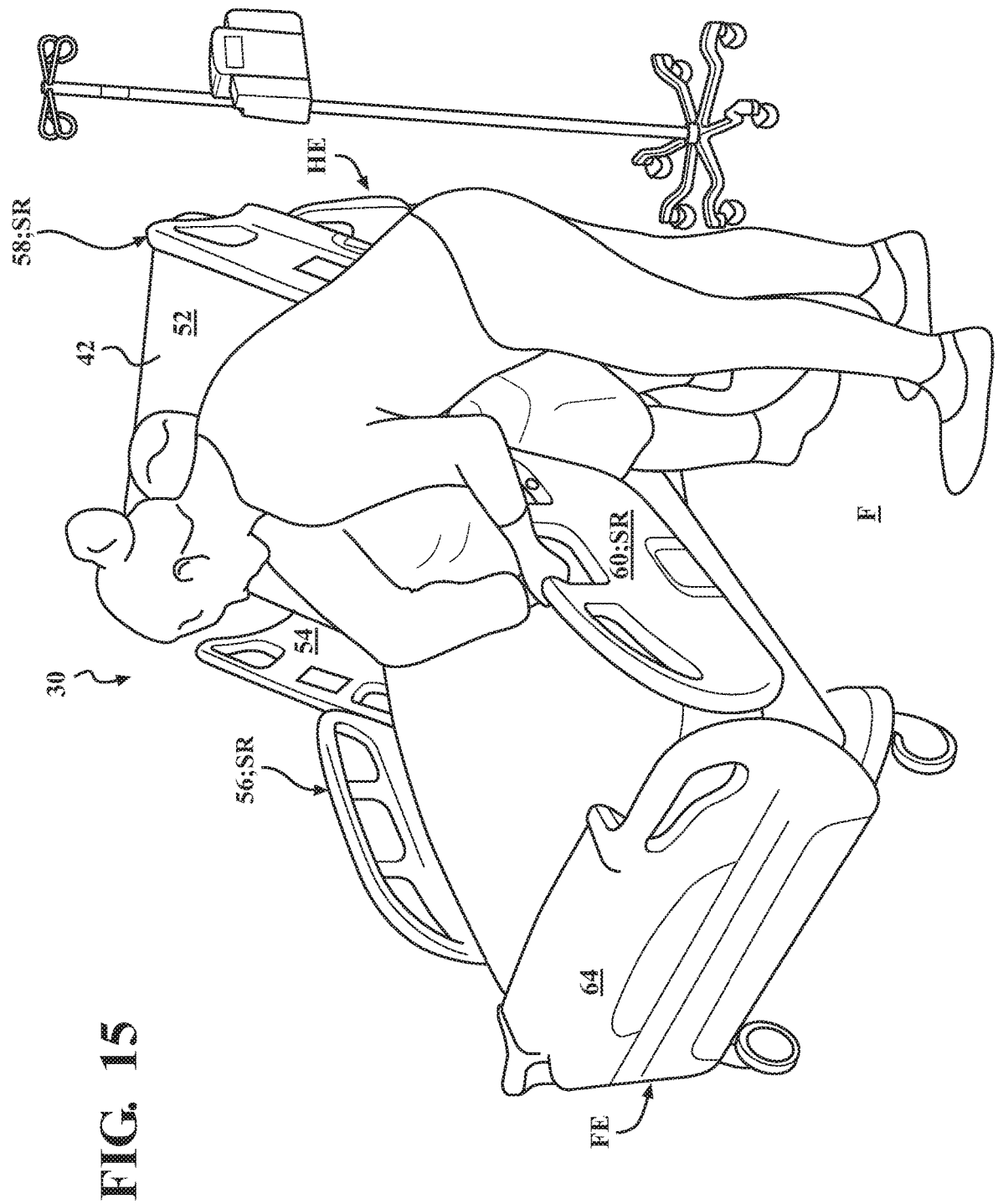
FIG. 15 is another perspective illustration of the patient and patient support apparatus of FIGS. 9-14, depicting the caregiver repositioning the foot-end side rail of the patient support apparatus with the patient seated between the head-end side rail and the foot-end side rail.

FIG. 14 depicts the caregiver swinging the patient's legs and feet off the patient support surface 42 so as to bring the patient into a seated position which, in turn, is depicted in FIG. 15. Here, when the controller 86 determines that the patient has moved into a seated position on the patient support surface 42, such as via the patient sensor 94 described above, the controller 86 subsequently activates the foot-end side rail indicator 92A to the first indication state I1 (not shown in FIGS. 14-15) so as to prompt the user to raise the fourth side rail 60 from the lowered side rail position SL (for example, to the raised side rail position SR or to the intermediate side rail position SI) so as to position the grip 66 of the fourth side rail 60 for use by the patient to facilitate patient egress.

Figure 16:
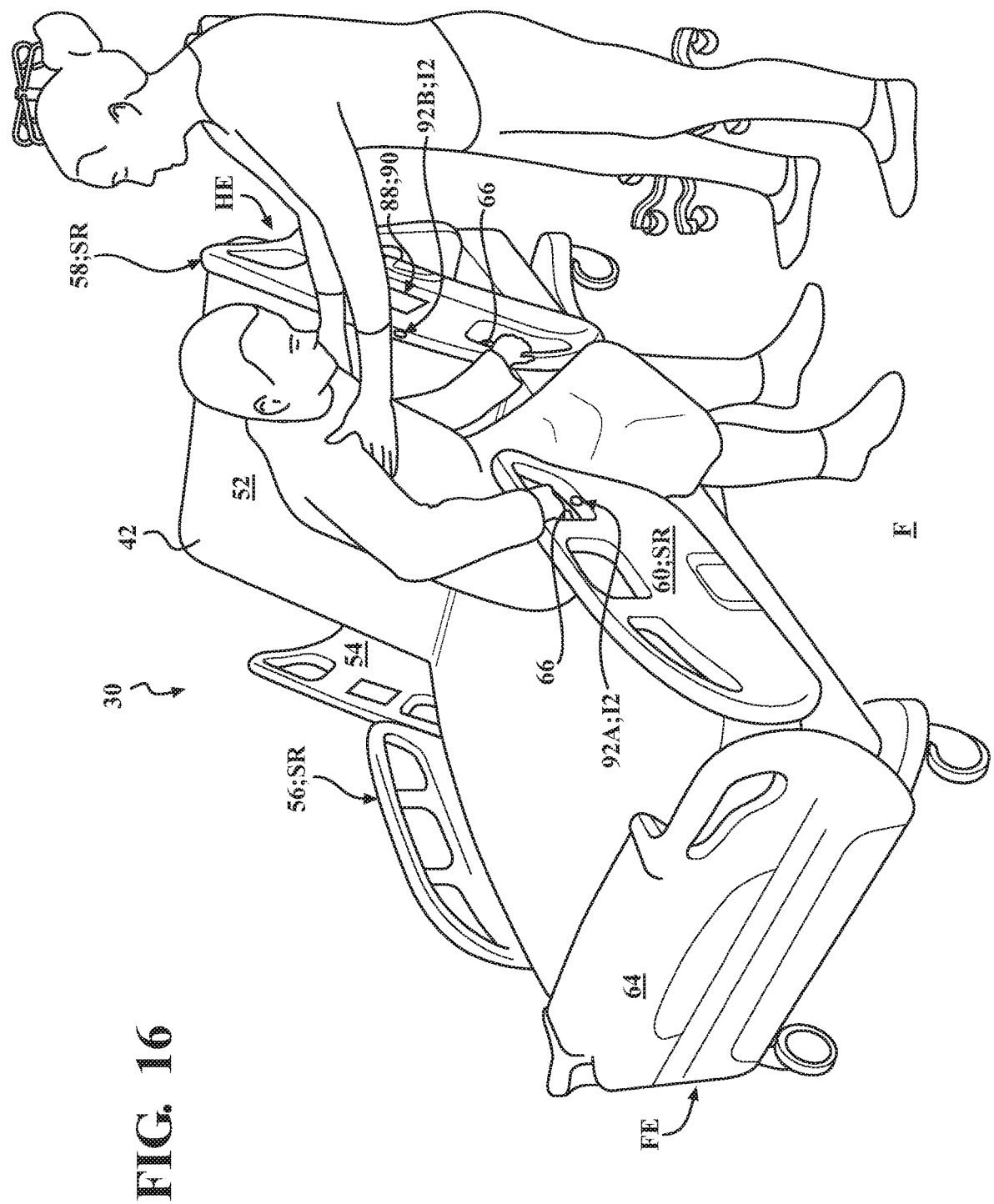
FIG. 16 is another perspective illustration of the patient and patient support apparatus of FIGS. 9-15, depicting the caregiver assisting the patient with ambulation to the floor surface from the patient support apparatus.
Figure 17:
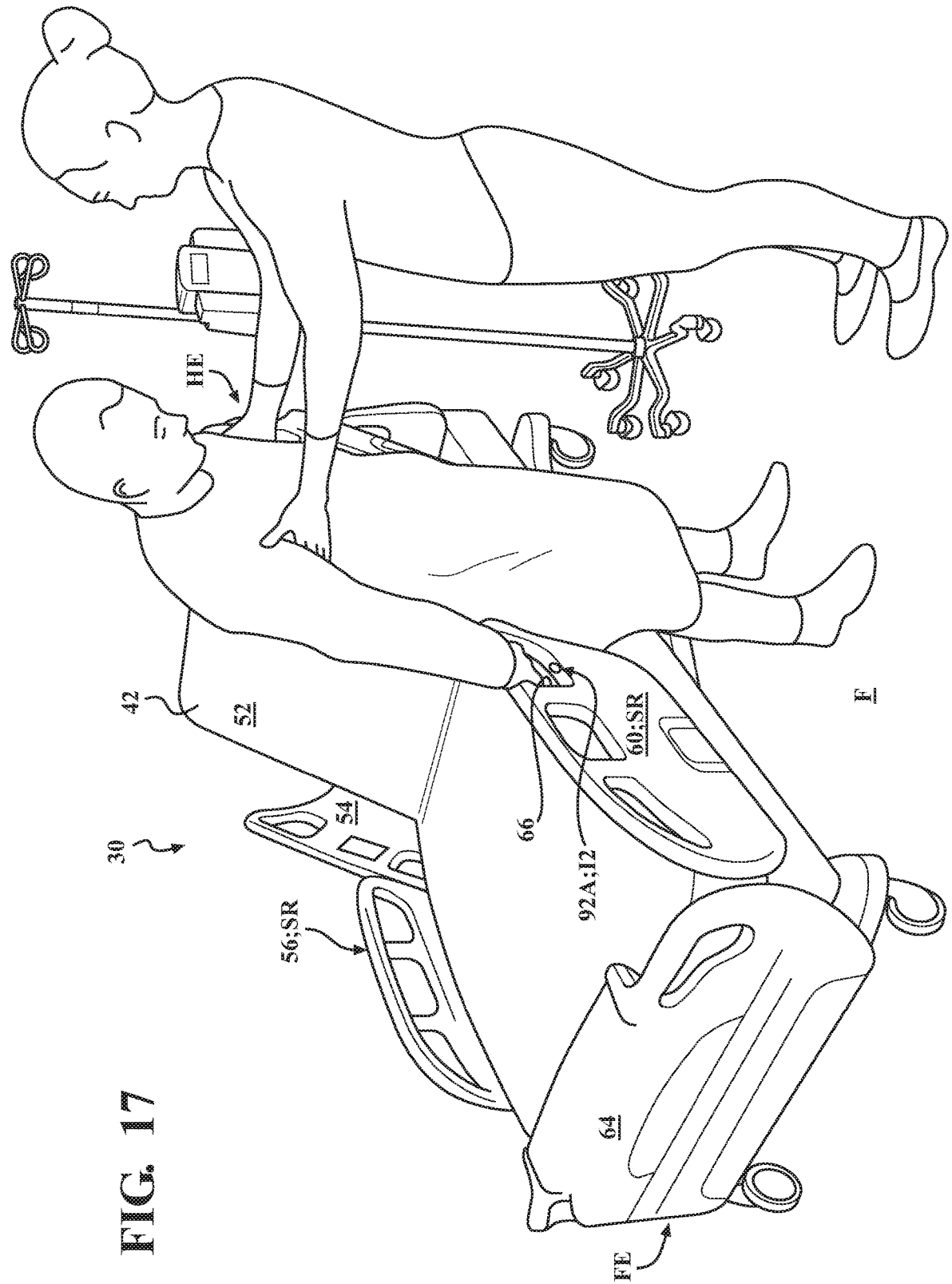
FIG. 17 is another perspective illustration of the patient and patient support apparatus of FIGS. 8-16, depicting the patient standing on the floor surface for ambulation away from the patient support apparatus.
Figure 18:
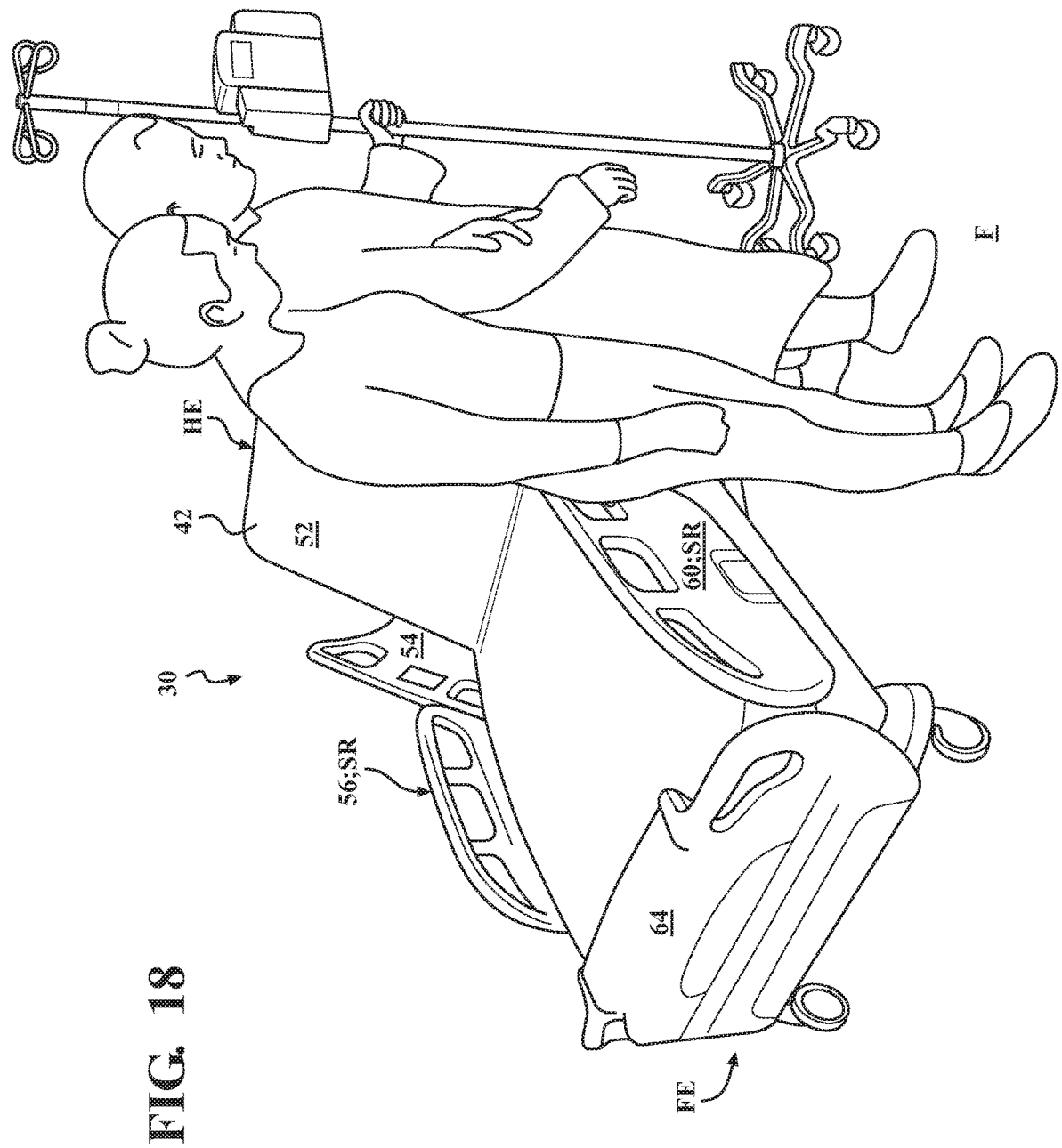
FIG. 18 is another perspective illustration of the patient and patient support apparatus of FIGS. 9-17, depicting the patient ambulating away from the patient support apparatus.

FIGS. 16-18 depict the patient grasping the grips 66 of the third and fourth side rails 58, 60 to help transition from the seated position (see FIG. 16) to a standing position (see FIG. 17) on the floor surface F, and then ambulating away from the patient support apparatus 30 (see FIG. 18). Here, while the caregiver is assisting the patient in egress from the seated position, both of the side rail indicators 92A, 92B are shown "off" in the second indication state I2. However, in one embodiment, the controller 86 is further configured to activate the side rail indicators 92A, 92B to "on" in the first indication state I1 after a predetermined period following when the patient sensor 94 determines that the patient has left the patient support deck 38. Here, by activating the side rail indicators 92A, 92B to "on" in the first indication state I1, or to some different indication state (for example, a different color, a different light intensity, and the like), the patient can be guided toward the grips 66 of the third and fourth side rails 58, 60 so as to facilitate subsequent ingress back to the patient support apparatus 30 at the correct location between the back section 44 and the leg section 48, as described in greater detail above. It will be appreciated that this configuration may be advantageously implemented where there is insufficient ambient light.

As noted above, those having ordinary skill in the art will appreciate that the process of completing subsequent ingress to the patient support apparatus 30 can occur by performing the general steps described above in connection with FIGS. 9-18 in reverse order. For example, once the patient has returned to the seated position, the controller 86 could activate the foot-end side rail indicator 92 so as to prompt the user to lower the fourth side rail 60 to allow room for swinging the patient's legs back onto the patient support surface 42.

In this way, the embodiments of the patient support apparatus 30 of the present disclosure afford significant opportunities for promoting patient egress and ambulation from the patient support surface 42 to the floor surface F, as well as for promoting patient ingress back to the patient support surface 42. Specifically, it will be appreciated that the arrangement of the egress lift configuration 72C and the egress deck configuration 78C advantageously positions the patient's feet close to the floor surface F while, at the same time, ensuring that the patient remains supported on the patient support surface 42. Furthermore, the arrangement of the ingress deck configuration 78D helps ensure that the patient is properly seated on the patient support surface 42 during ingress which, in turn, significantly minimizes re-positioning of the patient's body after ingress has been completed. Thus, injury and discomfort to the patient are reduced by minimizing re-positioning, and the caregiver can properly position the patient in a simple fashion without necessitating that the caregiver struggle to re-position the patient on the patient support surface 42. Further still, the embodiments of the patient support apparatus 30 described herein afford significant opportunities concerning usability by allowing caregivers to initiate patient egress with "one-touch" activation of the egress input 90A and, at the same time, ensuring that proper egress and/or ingress procedures are followed by guiding the caregiver through the requisite steps sequentially via activation of the indicators 92. Thus, the patient support apparatus 30 can be manufactured in a cost-effective manner while, at the same time, affording opportunities for improved functionality, features, and usability in connection with patient ambulation and mobility.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

What is claimed is:

1. A patient support apparatus comprising:
a base;
a patient support deck comprising deck sections movable relative to each other between a plurality of deck configurations including an egress deck configuration;
an articulation system coupled to said patient support deck to move said deck sections relative to one another;
a lift mechanism to move said patient support deck relative to said base between a plurality of lift configurations including an egress lift configuration;
an egress input arranged for actuation by a user;

a bed detection system configured to monitor data associated with a status of a patient supported on said patient support deck and to communicate said data with a remote monitoring station; and a controller in communication with said articulation system, said lift mechanism, said egress input, and said bed detection system, said controller being configured to interrupt communication of said bed detection system with said remote monitoring station, to drive said articulation system to move one or more of said deck sections to said egress deck configuration, and to drive said lift mechanism to move said patient support deck to said egress lift configuration in response to actuation of said egress input.

2. The patient support apparatus as set forth in claim 1, wherein said controller is further configured to restore communication between said bed detection system and said remote monitoring station after a predetermined period following patient egress.

3. The patient support apparatus as set forth in claim 1, further comprising a patient sensor in communication with said controller to detect a patient on said patient support deck; and
wherein said controller is configured to restore communication between said bed detection system and said remote monitoring station when said patient sensor subsequently determines the patient is supported by said patient support deck.

4. The patient support apparatus as set forth in claim 1, further comprising a resume input in communication with said controller and arranged for actuation by the user; and
wherein said controller is further configured to restore communication between said bed detection system and said remote monitoring station in response to actuation of said resume input.

5. The patient support apparatus as set forth in claim 1, wherein one of said deck sections of said patient support deck comprises a back section;
wherein said articulation system comprises a back deck actuator arranged to move said back section between a plurality of back rest configurations including a back egress configuration; and
wherein said controller is further configured to drive said back deck actuator to move said back section of said patient support deck to said back egress configuration in response to actuation of said egress input.

6. The patient support apparatus as set forth in claim 1, further comprising:
a head-end side rail arranged for movement between a lowered position and one or more raised positions, said head-end side rail comprising a head-end grip arranged to facilitate patient egress;
a head-end side rail sensor in communication with said controller to determine a position of said head-end side rail; and
a head-end side rail indicator in communication with said controller;
wherein said controller is further configured to activate said head-end side rail indicator when said patient support deck is in said egress lift configuration and in said deck egress configuration and when said head-end side rail sensor determines said head-end side rail is in an undesired position to prompt the user to move said head-end side rail to one of said raised positions to position said head-end grip for use by the patient so as to facilitate patient egress.

7. The patient support apparatus as set forth in claim 6, wherein said head-end side rail indicator is coupled to said head-end side rail for concurrent movement between said lowered and raised positions.

8. The patient support apparatus as set forth in claim 6, wherein said controller is further configured to activate said head-end side rail indicator at a first indication state when said head-end side rail sensor determines said head-end side rail is in said undesired position, and to activate said head-end side rail indicator at a second indication state when said head-end side rail sensor determines said head-end side rail is in one of said raised positions.

9. The patient support apparatus as set forth in claim 6, further comprising:
a patient sensor in communication with said controller to detect a patient on said patient support deck;
a foot-end side rail arranged for movement between a lowered position and one or more raised positions, said foot-end side rail comprising a foot-end grip arranged to facilitate patient egress;
a foot-end side rail sensor in communication with said controller to determine a position of said foot-end side rail; and
a foot-end side rail indicator in communication with said controller;
wherein said controller is further configured to activate said foot-end side rail indicator when said patient sensor determines said patient has moved to a seated position on said patient support deck and when said head-end side rail sensor determines said head-end side rail is in one of said raised positions to prompt the user to move said foot-end side rail to one of said raised positions to position said foot-end grip for use by the patient so as to facilitate patient egress.

10. The patient support apparatus as set forth in claim 9, wherein said controller is further configured to activate said foot-end side rail indicator and said head-end side rail indicator when said patient sensor determines the patient has left the patient support deck to guide the patient toward said head-end grip and said foot-end grip so as to facilitate subsequent patient ingress.

11. The patient support apparatus as set forth in claim 9, wherein said controller is further configured to activate said foot-end side rail indicator when said patient sensor determines the patient has subsequently moved to a seated position on said patient support deck following egress and when said foot-end side rail is in one of said raised positions to prompt the user to move said foot-end side rail to said lowered position to facilitate transitioning the patient from the seated position to a flat position on said patient support deck.

12. The patient support apparatus as set forth in claim 1, further comprising:
a side rail arranged for movement between a lowered position and one or more raised positions;
a side rail sensor in communication with said controller to determine a position of said side rail; and
a side rail indicator in communication with said controller;
wherein said controller is further configured to activate said side rail indicator when said patient support deck is in said egress lift configuration and in said deck egress configuration and when said side rail sensor determines said rail is in an undesired position to prompt the user to move said side rail to said lowered position so as to facilitate patient egress.

13. A patient support apparatus comprising:
a base;
an intermediate frame defining a head end and a foot end;
a lift mechanism to move said intermediate frame relative to said base between one or more head-end positions including an egress head-end position and to move said intermediate frame relative to said base between one or more foot-end positions including an egress foot-end position;
a patient support deck operatively attached to said intermediate frame and having a back section arranged for movement relative to said intermediate frame and a leg section arranged for movement relative to said intermediate frame;
a back deck actuator arranged to move said back section relative to said intermediate frame between a plurality of back rest configurations including a back egress configuration;
a leg deck actuator arranged to move said leg section relative to said intermediate frame between a plurality of leg rest configurations including a leg egress configuration;
an egress input arranged for actuation by a user;
a bed detection system configured to monitor data associated with a status of a patient supported on said patient support deck and to communicate said data with a remote monitoring station; and
a controller in communication with said lift mechanism, said back deck actuator, said leg deck actuator, and said egress input, said controller being configured to drive said lift mechanism to move said head end of said intermediate frame to said egress head-end position and to move said foot end of said intermediate frame to said egress foot-end position lower than said egress head-end position, drive said back deck actuator to move said back section of said patient support deck to said back egress configuration, drive said leg deck actuator to move said leg section of said patient support deck to said leg egress configuration, and interrupt communication of said bed detection system with said remote monitoring station in response to actuation of said egress input.

14. The patient support apparatus as set forth in claim 13, wherein said leg section is substantially parallel with a floor surface supporting said base when said head end is in said egress head-end position, said foot end is in said egress foot-end position, said back section is in said back egress configuration, and said leg section is in said leg egress configuration.

15. The patient support apparatus as set forth in claim 13, wherein said foot end of said intermediate frame is closer to a floor surface supporting said base than said back section of said patient support deck when said head end is in said egress head-end position, said foot end is in said egress foot-end position, said back section is in said back egress configuration, and said leg section is in said leg egress configuration.

16. The patient support apparatus as set forth in claim 13, wherein said lift mechanism comprises:
a head-end lift actuator to move said head end of said intermediate frame relative to said base between said one or more head-end positions; and
a foot-end lift actuator to move said foot end of said intermediate frame relative to said base between said one or more foot-end positions; and
wherein said controller is configured to drive said head-end lift actuator to move said head end of said intermediate frame to said egress head-end position, and to drive said foot-end lift actuator to move said foot end of said intermediate frame to said egress foot-end position lower than said egress head-end position, in response to actuation of said egress input.

17. The patient support apparatus as set forth in claim 16, wherein said controller is configured to, in response to actuation of said egress input, independently and sequentially drive two or more of: said back deck actuator, said leg deck actuator, said head-end lift actuator, and said foot-end lift actuator.

18. The patient support apparatus as set forth in claim 17, wherein said controller is configured to drive said leg deck actuator to move said leg section of said patient support deck to said leg egress configuration prior to driving said foot-end lift actuator and said head-end lift actuator.

19. The patient support apparatus as set forth in claim 16, wherein said controller is configured to, in response to actuation of said egress input, simultaneously drive two or more of: said back deck actuator, said leg deck actuator, said head-end lift actuator, and said foot-end lift actuator.

20. The patient support apparatus as set forth in claim 19, wherein said controller is configured to drive each of said back deck actuator, said leg deck actuator, said head-end lift actuator, and said foot-end lift actuator at independent drive speeds to effect coordinated motion to said egress head-end position, said egress foot-end position, said back egress configuration, and said leg egress configuration.

21. The patient support apparatus as set forth in claim 19, wherein said controller is configured to drive each of said back deck actuator, said leg deck actuator, said head-end lift actuator, and said foot-end lift actuator at independent drive speeds such that movement into at least two of said egress head-end position, said egress foot-end position, said back egress configuration, and said leg egress configuration occurs substantially simultaneously.

22. A patient support apparatus comprising:
a base;
a patient support deck supported by said base and having a back section and a leg section arranged for movement relative to said back section;
a back deck actuator arranged to move said back section between a plurality of back rest configurations including a back egress configuration;
a leg deck actuator arranged to move said leg section between a plurality of leg rest configurations including a leg egress configuration and a leg ingress configuration;
a patient sensor to detect a patient on said patient support deck;
an egress input arranged for actuation by a user; and
a controller in communication with said back deck actuator, said leg deck actuator, and said egress input, wherein said controller is configured to drive said back deck actuator to move said back section to said back egress configuration and to drive said leg deck actuator to move said leg section to said leg egress configuration in response to actuation of said egress input; and
wherein said controller is further configured to subsequently drive said leg deck actuator to move said leg section from said leg egress configuration to said leg ingress configuration after a predetermined period where said patient sensor detects an absence of the patient on said patient support deck.

* * * * *